US009314229B2

(12) United States Patent
Argentine

(10) Patent No.: US 9,314,229 B2
(45) Date of Patent: Apr. 19, 2016

(54) SUTURING DEVICE AND METHOD FOR SEALING AN OPENING IN A BLOOD VESSEL OR OTHER BIOLOGICAL STRUCTURE

(71) Applicant: Medtronic Vascular, Inc., Santa Rosa, CA (US)

(72) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 698 days.

(21) Appl. No.: 13/802,563

(22) Filed: Mar. 13, 2013

(65) Prior Publication Data
US 2014/0276976 A1 Sep. 18, 2014

(51) Int. Cl.
*A61B 17/04* (2006.01)
*A61B 17/00* (2006.01)
A61B 17/06 (2006.01)

(52) U.S. Cl.
CPC ......... *A61B 17/0057* (2013.01); *A61B 17/0469* (2013.01); *A61B 17/0482* (2013.01); *A61B 2017/00477* (2013.01); *A61B 2017/00663* (2013.01); *A61B 2017/00862* (2013.01); *A61B 2017/0472* (2013.01); *A61B 2017/06052* (2013.01)

(58) Field of Classification Search
CPC ........... A61B 17/0057; A61B 17/0469; A61B 17/00862; A61B 2017/0472; A61B 2017/06052; A61B 2017/00663; A61B 2017/00477; A61B 17/0482
See application file for complete search history.

(56) References Cited

U.S. PATENT DOCUMENTS

| 5,304,184 | A | 4/1994 | Hathaway et al. |
| 5,476,469 | A | 12/1995 | Hathaway et al. |
| 5,720,757 | A | 2/1998 | Hathaway et al. |
| 5,810,850 | A | 9/1998 | Hathaway et al. |
| 5,820,631 | A | 10/1998 | Nobles |
| 5,860,990 | A | 1/1999 | Nobles et al. |

(Continued)

FOREIGN PATENT DOCUMENTS

| AU | 2003212025 | 3/2006 |
| AU | 2006251579 | 5/2006 |

(Continued)

OTHER PUBLICATIONS

WO2014-018725, PCT Search Report and Written Opinion, mailed Jun. 2, 2014.

(Continued)

*Primary Examiner* — Ryan J Severson
*Assistant Examiner* — Rachel S Papeika

(57) ABSTRACT

A suturing device includes a handle, an elongated body, at least one suture snag, at least one pair of needles, and at least one suture pair. The suture snag is moveable between a deployed position in which two distal arm portions thereof radially extend away from the elongated body and a retracted position in which the two distal arm portions are disposed within the elongated body. The suture pair is slidingly disposed through the needle pair. The suturing device deploys the suture snag within a vessel adjacent to an arteriotomy, extends the needle pair through a vessel wall around the arteriotomy and through the deployed suture snag, extends the suture pair beyond the distal ends of the needle pair, and then utilizes the suture snag to capture the extended suture pair by retracting the suture snag to pull first or distal ends of the sutures back into the suturing device.

20 Claims, 27 Drawing Sheets

(56) References Cited

U.S. PATENT DOCUMENTS

| | | |
|---|---|---|
| 6,117,144 A | 9/2000 | Nobles et al. |
| 6,132,440 A | 10/2000 | Hathaway et al. |
| 6,245,079 B1 | 6/2001 | Nobles et al. |
| 6,348,059 B1 | 2/2002 | Hathaway et al. |
| 6,551,331 B2 | 4/2003 | Nobles et al. |
| 6,562,052 B2 | 5/2003 | Nobles et al. |
| 6,733,509 B2 | 5/2004 | Nobles et al. |
| 6,911,034 B2 | 6/2005 | Nobles et al. |
| 7,004,952 B2 | 2/2006 | Nobles et al. |
| 7,060,078 B2 | 6/2006 | Hathaway et al. |
| 7,090,686 B2 | 8/2006 | Nobles et al. |
| 7,670,349 B2 | 3/2010 | Hathaway et al. |
| 7,686,821 B2 | 3/2010 | Hathaway et al. |
| 7,803,167 B2 | 9/2010 | Nobles et al. |
| 7,905,892 B2 | 3/2011 | Nobles et al. |
| 8,197,497 B2 | 6/2012 | Nobles et al. |
| 8,197,510 B2 | 6/2012 | Nobles |
| 8,246,636 B2 | 8/2012 | Nobles et al. |
| 8,348,962 B2 | 1/2013 | Nobles et al. |
| 2004/0068273 A1 | 4/2004 | Fariss et al. |
| 2005/0228407 A1 | 10/2005 | Nobles |
| 2006/0030868 A1 | 2/2006 | Bennett |
| 2007/0225744 A1 | 9/2007 | Nobles |
| 2007/0276414 A1 | 11/2007 | Nobles |
| 2009/0062852 A1 | 3/2009 | Marino |
| 2010/0030242 A1 | 2/2010 | Nobles et al. |
| 2011/0270282 A1 | 11/2011 | Lemke |

FOREIGN PATENT DOCUMENTS

| | | |
|---|---|---|
| AU | 2006262498 | 6/2006 |
| CA | 2323084 | 12/2006 |
| EP | 941698 | 5/2005 |
| EP | 1570790 | 11/2008 |
| EP | 2011441 | 1/2009 |
| JP | 2009144590 | 2/1999 |
| JP | 2007533759 | 9/2005 |
| JP | 2008513600 | 5/2006 |
| JP | 2008517194 | 6/2006 |
| JP | 2010501228 | 3/2008 |
| WO | WO2006/037039 | 4/2006 |
| WO | WO2006/127636 | 11/2006 |
| WO | WO2007/001936 | 1/2007 |
| WO | WO2008/121738 | 10/2008 |
| WO | WO2009/137766 | 11/2009 |

OTHER PUBLICATIONS

U.S. Appl. No. 61/229,297, filed Jan. 28, 2010, Nobles.

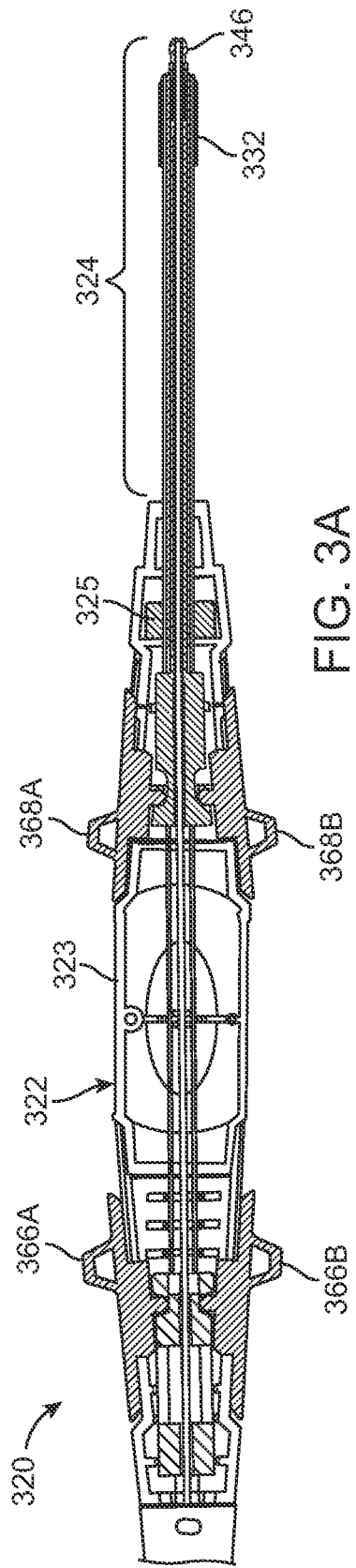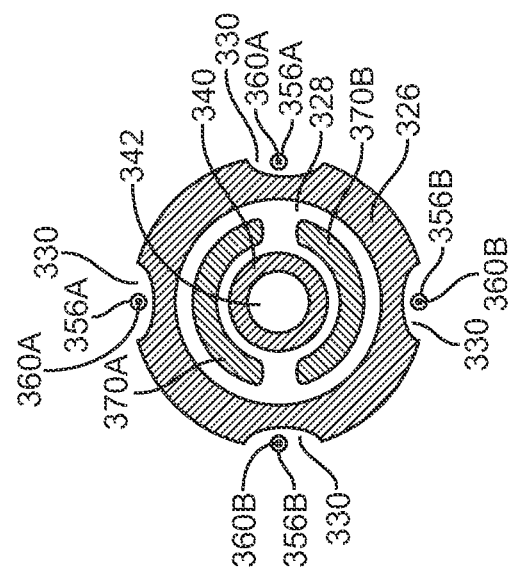

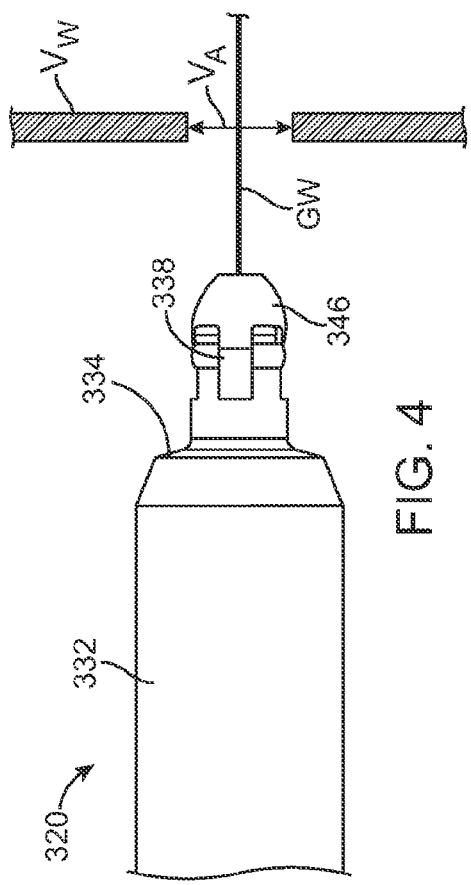
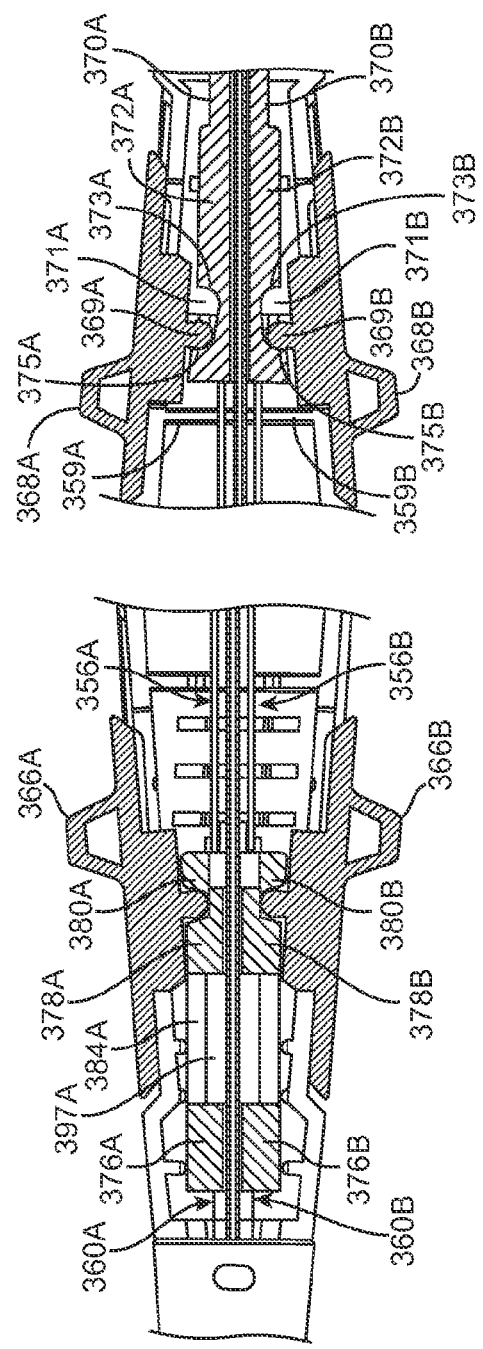
FIG. 4
FIG. 4A
FIG. 4B

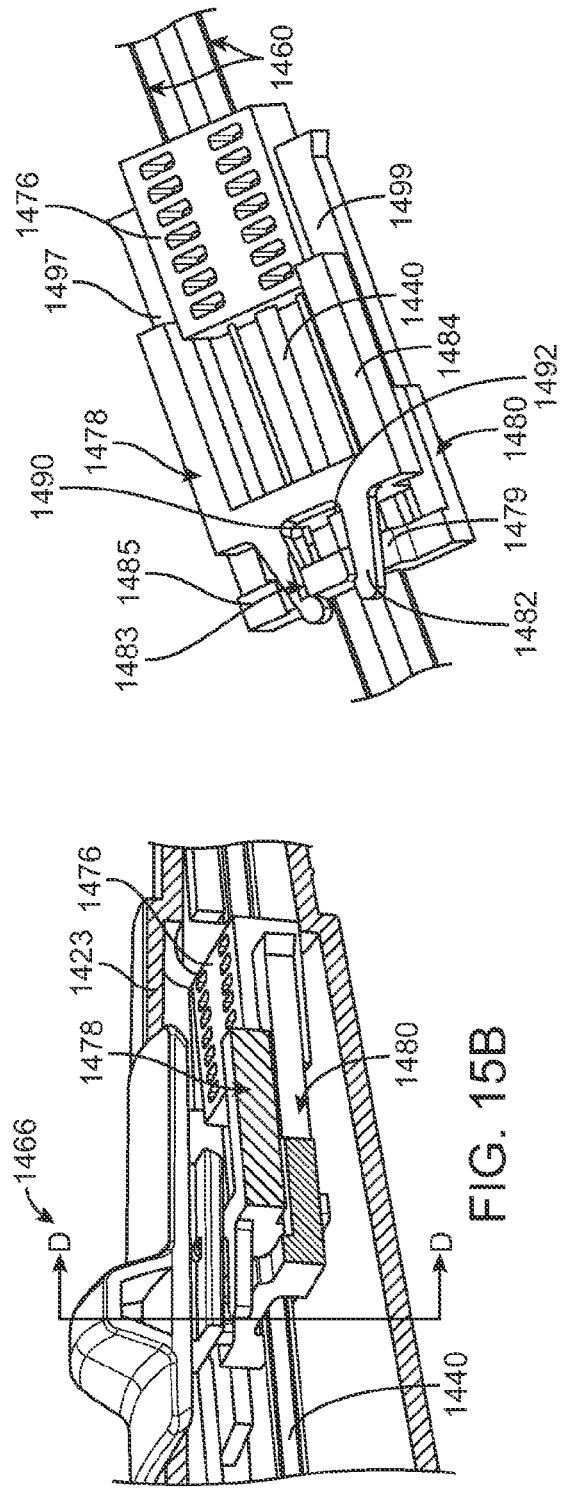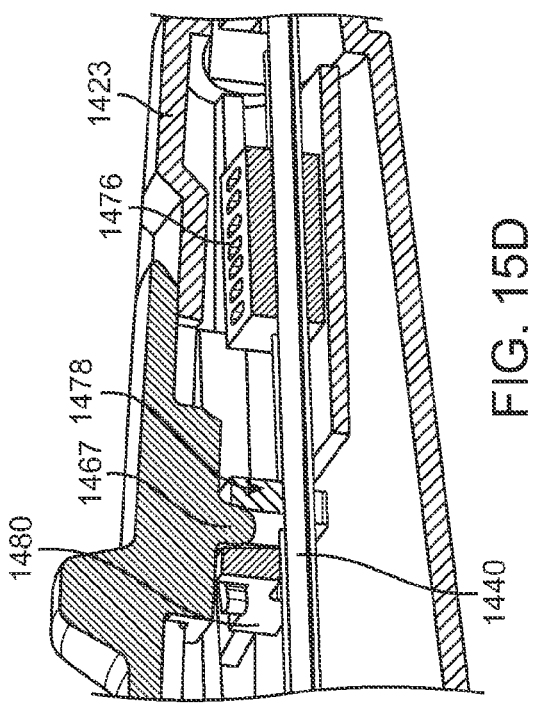

SUTURING DEVICE AND METHOD FOR SEALING AN OPENING IN A BLOOD VESSEL OR OTHER BIOLOGICAL STRUCTURE

FIELD OF THE INVENTION

The present invention relates to medical suturing devices, and more particularly, to suturing devices for closing an opening in an arterial or other biological tissue wall that is not directly accessible to a user.

BACKGROUND OF THE INVENTION

Various cardiovascular procedures, such as angioplasty, stent placement and atherectomy, require gaining access to the vasculature. With reference to FIGS. 1 and 2, access to the vasculature of a patient 100 typically is through the femoral artery and is percutaneous, involving insertion of a needle (not shown), and in some cases a dilator (not shown), in the region of the groin to form a track 104 through subcutaneous tissue 106 and to puncture and create an arteriotomy $V_A$ in a vessel wall $V_W$ of the femoral artery. A guidewire GW is then advanced through the needle and into the femoral artery. The needle and dilator, if present, are then removed. A catheter or other interventional device 102 is then advanced over the guidewire GW, along the track 104 and into the femoral artery in order to perform the selected procedure.

The size of the puncture opening in the artery corresponds to the size of the catheter or interventional device used, and such devices may typically range in diameter from 5 French for a diagnostic procedure to 6-20 French for a therapeutic procedure. In some cases, medical suturing systems are utilized to "pre-close" the arteriotomy $V_A$ by positioning one or more stitches adjacent to interventional device 102 that result in hemostasis of the arteriotomy $V_A$ around the interventional device 102 during the procedure. After the procedure is completed and the interventional device(s) are removed, the stitches positioned by the medical suturing system are utilized to fully close the arteriotomy $V_A$.

In other cases, i.e., when the size of the arteriotomy is relatively small, such pre-closure is not required and a medical suturing system or other technique is utilized to close the arteriotomy after the interventional device(s) are removed. A number of other techniques are known to facilitate closure and healing of the arteriotomy. One technique includes application of pressure at the puncture site for a relatively extended length of time. More particularly, compression has traditionally been applied to the puncture site for at least 30-45 minutes for the wound to close naturally after removal of the catheter. Patients are required to remain lying down, essentially motionless and often with a heavy sandbag placed on their upper leg, for several hours to ensure that the bleeding has stopped. The recovery time from the medical procedure may be as little as half of an hour, but the recovery time from the wound can exceed twenty-four hours. Longer recovery times may result in increased expenses, increased patient discomfort, and greater the risk of complications. Other approaches to arteriotomy closure include a compression clamp device, a thrombotic or collagen plug, biological adhesives adapted to seal the arteriotomy, and/or stapling devices.

Medical suturing systems that have been proposed facilitate closure and healing of the arteriotomy and resolve some of the concerns associated with arteriotomy closure during and after vascular catheterization procedures. However, a need in the art still exists for a medical suturing system that consistently and reliably facilitates closure and healing of the arteriotomy.

BRIEF SUMMARY OF THE INVENTION

Embodiments hereof are also related to a method of positioning a suture at an arteriotomy of a vessel wall of a vessel. A distal end of a suturing device is positioned through the arteriotomy. The suturing device includes a handle and an elongated body coupled to a distal end of the handle. At least one suture snag of the suturing device is deployed within the vessel from a retracted position in which two distal arm portions thereof are disposed within the elongated body to a deployed position in which the two distal arm portions radially extend away from the elongated body. At least one pair of needles of the suturing device are distally advanced from a loaded position in which the pair of needles is disposed within the elongated body to a deployed position in which the pair of needles distally extend away from a distal end of the elongated body and penetrate through the vessel wall and through apertures in the two distal arms portions of the deployed suture snag. A suture is slidingly disposed through the lumen of each needle, and each suture is concurrently carried with its respective needle during the step of extending the pair of needles to the deployed position. While the pair of needles remain in the deployed position, the sutures disposed therein are distally advanced relative to their respective needles from a loaded position in which a first end of each suture is disposed within its respective needle to a deployed position in which the first end of each suture extends distally away from the distal end of its respective needle.

According to another embodiment hereof, a method of positioning a suture at an arteriotomy of a vessel wall of a vessel includes positioning a distal end of a suturing device through the arteriotomy. The suturing device includes a handle having a suture holder and a needle holder disposed within the handle, and an elongated body coupled to a distal end of the handle. At least one suture snag of the suturing device is deployed within the vessel from a retracted position in which two distal arm portions of the suture snag are disposed within the elongated body to a deployed position in which the two distal arm portions radially extend away from the elongated body. A pair of needles of the suturing device is distally advanced from a loaded position in which the pair of needles is disposed within the elongated body to a deployed position in which the pair of needles distally extend from a distal end of the elongated body. The pair of needles is coupled to the needle holder and a suture is slidingly disposed through the lumen of each needle. A first end of each suture is disposed within its respective needle when the needle is in the loaded position. The sutures are coupled to the suture holder when the needles are in the loaded and deployed positions such that each suture is concurrently carried with its respective needle during the step of distally advancing the pair of needles to the deployed position. The sutures are distally advanced from a loaded position in which each first end of each suture is disposed within its respective needle to a deployed position in which the first ends of each suture extends distally away from the distal end of their respective needle. The sutures are coupled to the suture holder and the needles remain in their deployed position during the step of distally advancing the sutures.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3A is a sectional view of FIG. 3 taken along line A-A.

FIG. 3B is a cross-sectional view of FIG. 3 taken along line B-B.

FIG. 4 is a side view illustration of a first step of a method of using the suturing device of FIG. 3 according to an embodiment hereof, wherein the suturing device is advanced towards an arteriotomy.

FIG. 4A is a sectional view of a proximal portion of handle of the suturing device of FIG. 3, wherein the handle portion includes actuation mechanisms for deploying the needles and sutures with the actuation mechanisms being shown in a first or loaded position.

FIG. 4B is a sectional view of a distal portion of handle of the suturing device of FIG. 3, wherein the handle portion includes actuation mechanisms for deploying the suture snags and the actuation mechanisms are shown in a retracted position.

FIG. 15B is an enlarged sectional view of a proximal portion of the handle of FIG. 15 illustrating an actuation mechanism for deploying the needles and the sutures associated therewith.

FIG. 15C is a perspective top view of the actuation mechanism of FIG. 15B, wherein the housing of the handle is shown in phantom.

FIG. 15D is a sectional view taken along line D-D of FIG. 15B.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of an arteriotomy, which is used herein to refer to an opening, cut, or incision of an artery, the invention may also be used in any other blood vessels or body passageways where it is deemed useful. For example, the device could be used to suture openings or incisions of other tissue such as a patent ductus arteriosus, a patent foramen ovale, a heart defect, a puncture wound, and the like. Furthermore, there is no intention to be bound by any expressed or implied theory presented in the preceding technical field, background, brief summary or the following detailed description.

Figure 12:
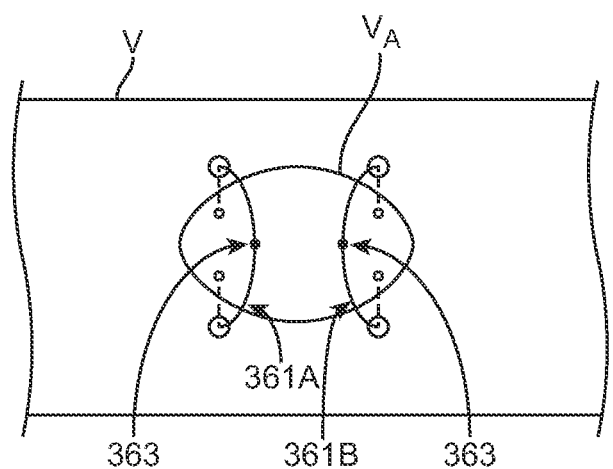
FIG. 12 is a top view illustration of another step of a method of use according to an embodiment hereof, wherein sutures having ends fastened together extend through the vessel wall around the arteriotomy.
Figure 13:
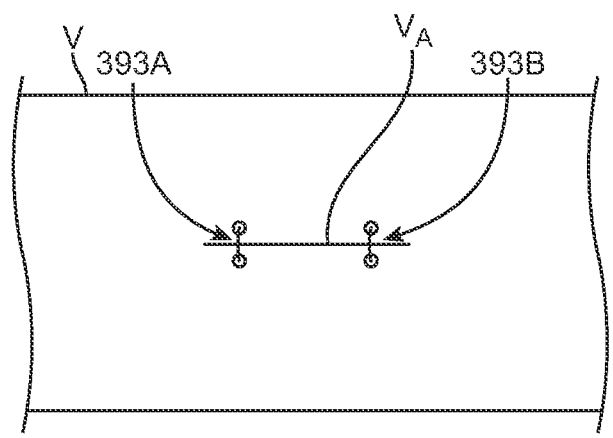
FIG. 13 is a top view illustration of another step of a method of use according to an embodiment hereof, wherein tension applied to the coupled sutures closes the arteriotomy.
Figure 14:
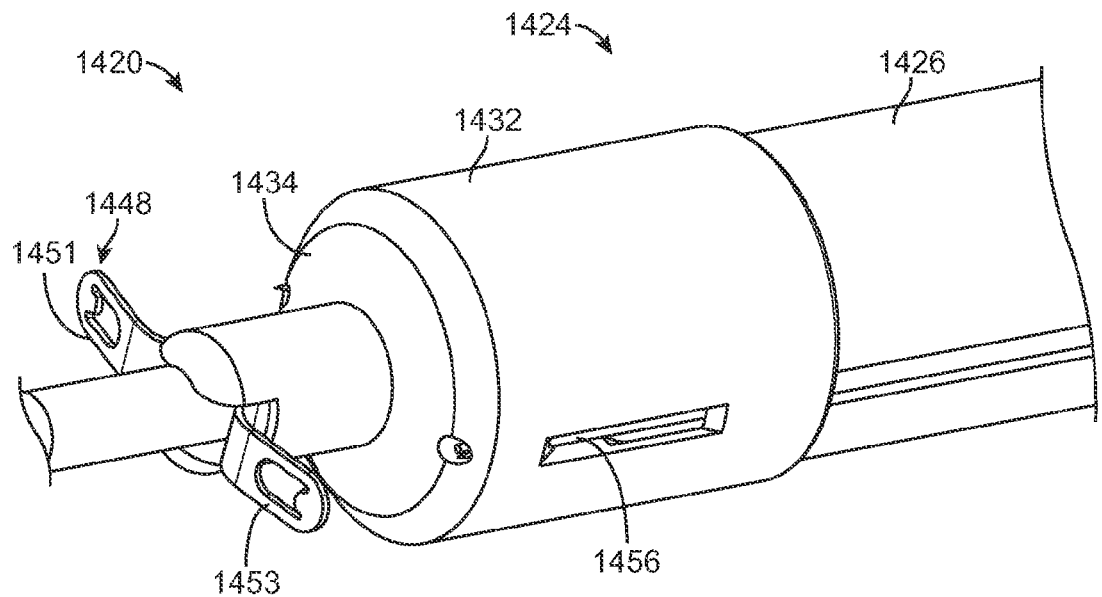
FIG. 14 is a perspective view of a distal end of a suturing device according to another embodiment hereof, wherein the suturing device includes only a single suture snag and a pair of needles for positioning a pair of sutures.
Figure 15:
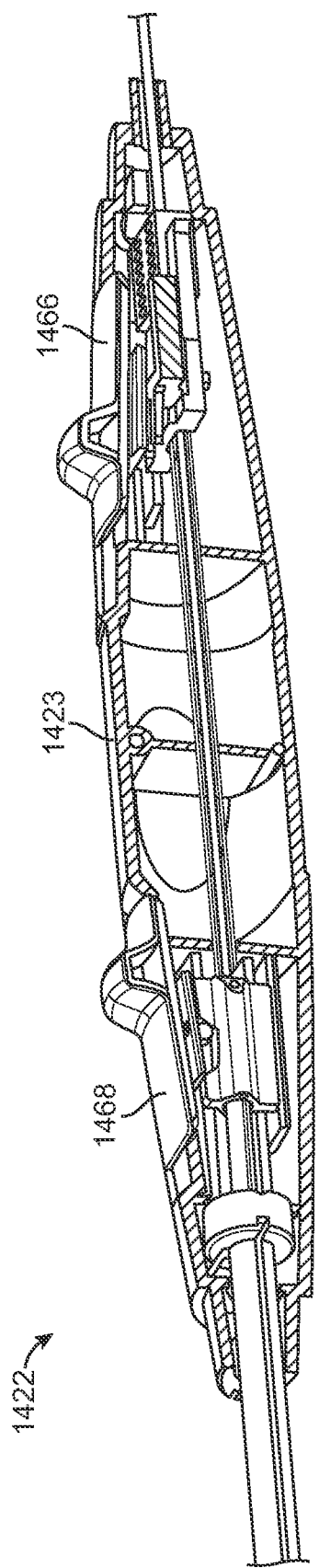
FIG. 15 is a sectional view of a handle of the suturing device of FIG. 14.

Suturing devices according to embodiments hereof use a pair of needle to position a pair of sutures beyond the boundaries or perimeter of an arteriotomy and then utilize a suture snag to capture the ends of the sutures and pull the suture ends back into the suturing device. The captured sutures are then tied together to form a single stitch. The suturing devices may be used to seal a blood vessel during and/or following an interventional catheterization procedure. As will be understood by one of ordinary skill in the art, the number of suture snags and needles may vary depending upon the number of sutures being positioned by the suturing device. For instance, one suture snag and one pair of needles are utilized for positioning one pair of sutures at an arteriotomy, whereby the suture pair is then tied together to form a single stitch, while two suture snags and two pairs of needles are utilized for positioning two pairs of sutures at an arteriotomy, whereby each suture pair is then tied together to form a total of two stitches. During delivery thereof, a first suture of a suture pair is housed within a first needle of a needle pair and a second suture of the suture pair is housed within a second needle of the needle pair. The first and second needles of the needle pair actuate or move together. Thus, a plurality of needles with a complementing number of suture snags may be incorporated into the device to accomplish the specific needs of the application. The embodiment of FIGS. 3-13 illustrate a suturing device for positioning two suture pairs for forming a total of two stitches at an arteriotomy while the embodiment of FIGS. 14-15 illustrate a suturing device for positioning one suture pair for forming a single stitch at an arteriotomy.

More particularly, a suturing device 320 for suturing arterial vessel walls and other biological tissue is shown in FIGS. 3-13. With initial reference to FIGS. 3, 3A, and 3B, suturing device 320 according to one embodiment includes first and second needle pairs 356A, 356B and first and second suture snags 348A, 348B for positioning and capturing respective ends of first and second suture pairs 360A, 360B beyond the boundaries of the arteriotomy. Suturing device 320 includes an inner or guidewire shaft 340 as well as suture pairs 360A, 360B extending proximally from a handle 322 and an elongated body 324 extending distally from handle 322. Handle 322 includes first and second sliders or actuators 366A, 366B which are utilized to extend needle pairs 356A, 356B, respectively, and suture pairs 360A, 360B, respectively, as will be described in more detail herein, and third and fourth sliders or actuators 368A, 368B which are utilized to deploy suture snags 348A, 348B, respectively, as will be described in more detail herein. More particularly, first suture pair 360A and first needle pair 356A are independently deployed or controlled by first actuator 366A of a first needle and suture pair actuation mechanism of handle 322, and second suture pair 360B and second needle pair 356B are independently deployed or controlled by opposing second actuator 366B of a second needle and suture pair actuation mechanism of handle 322. As such, a user may choose to deploy only one needle pair within a vessel at a time, for example when the vessel is of a relatively smaller size, or may choose to deploy both needle pairs simultaneously. In addition, each actuator 366A, 366B and corresponding actuation mechanism is provided for the deployment of two components, i.e., a pair of needles and the respective suture pair held thereby, which is beneficial for ease of use.

Elongated body 324 includes an outer shaft 326 and a distal guiding component 332 which is disposed over and coupled to a distal portion of outer shaft 326. Distal guiding component 332 may be coupled to outer shaft 326 by adhesive or a threaded connection, or may be unitary or integral with the outer shaft. A distal end of distal guiding component 332 defines the distal end of elongated body 324. Each of the outer shaft and the distal guiding component are hollow tubular components and collectively define at least one continuous lumen 328 through elongated body 324 for housing two elongated transmission members 370A, 370B and inner shaft 340, as shown in the sectional view of FIG. 3B. As will be explained in more detail herein, transmission members 370A, 370B extend between third and fourth actuators 368A, 368B, respectively, and suture snags 348A, 348B, respectively, and function as actuation mechanisms for the suture snags because they interact with third and fourth actuators 368A, 368B, respectively, in the deployment and retraction of the suture snags. Inner shaft 340 extends through handle 332 to a tapered distal tip or nosecone 346, which is coupled to a distal end portion 345 (shown in FIG. 4D) of inner shaft 340. Inner shaft 340 and distal tip 346 may define a continuous lumen 342 for tracking suturing device 320 over a guidewire (not shown). As shown in the sectional view of FIG. 3A, a hemostasis seal 325 is disposed with handle 322 around inner shaft 340 adjacent to a proximal end of outer shaft 326.

Since suturing device 320 is utilized to place the sutures around the border or edge of an arteriotomy of a vessel, the components of the suturing device will be described while simultaneously describing a method of using the suturing device to position suture pairs 360A, 360B in situ with reference to FIGS. 4-13. Referring to FIG. 4, a side view of a distal end portion of suturing device 320 having suture pairs 360A, 360B loaded therein is shown being distally advanced over a guidewire GW towards an arteriotomy $V_A$ in the vessel wall $V_W$ of a vessel. In an embodiment, each suture of suture pairs 360A, 360B is a continuous strand or filament of material having a first end 362A, 362B, respectively (see FIG. 4E) and a second end 364A, 364B, respectively (see FIG. 3). Exemplary suture materials include but are not limited to a monofilament or plastic suture material, such as polypropylene. Suturing device 320 is in a delivery configuration, in which suture snags 348A, 348B are in a retracted position while needles pairs 356A, 356B and suture pairs 360A, 360B are in a loaded position.

Figure 1:
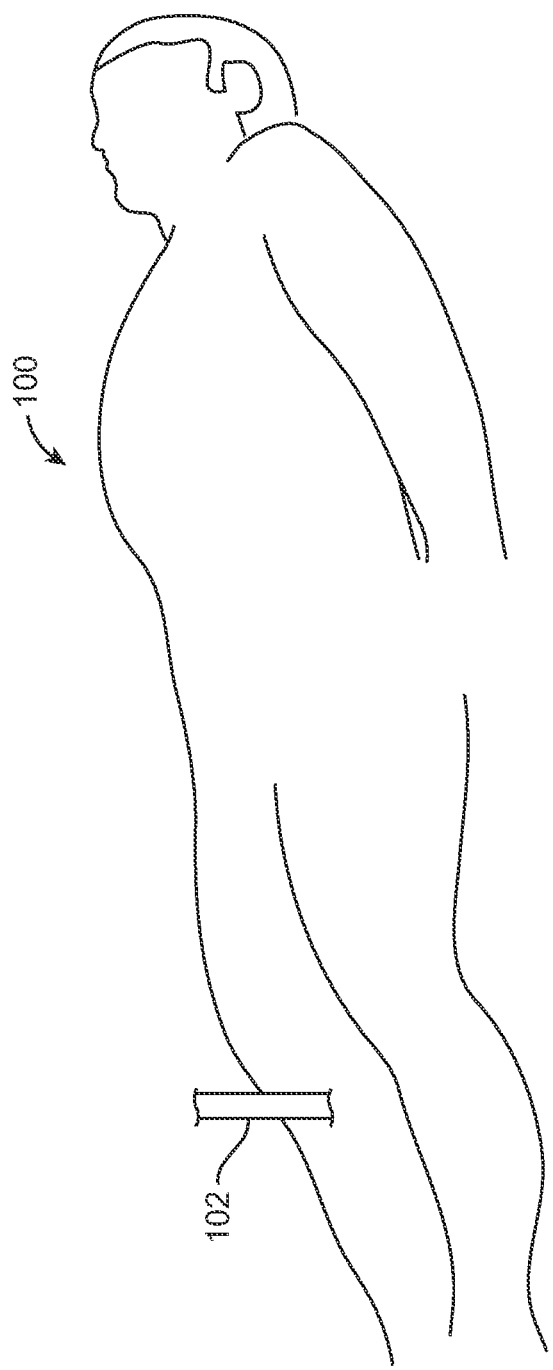
FIGS. 1 and 2 illustrate the introduction of an introducer sheath into the vasculature via the femoral artery, thereby forming an arteriotomy in a vessel wall of the femoral artery.
Figure 2:
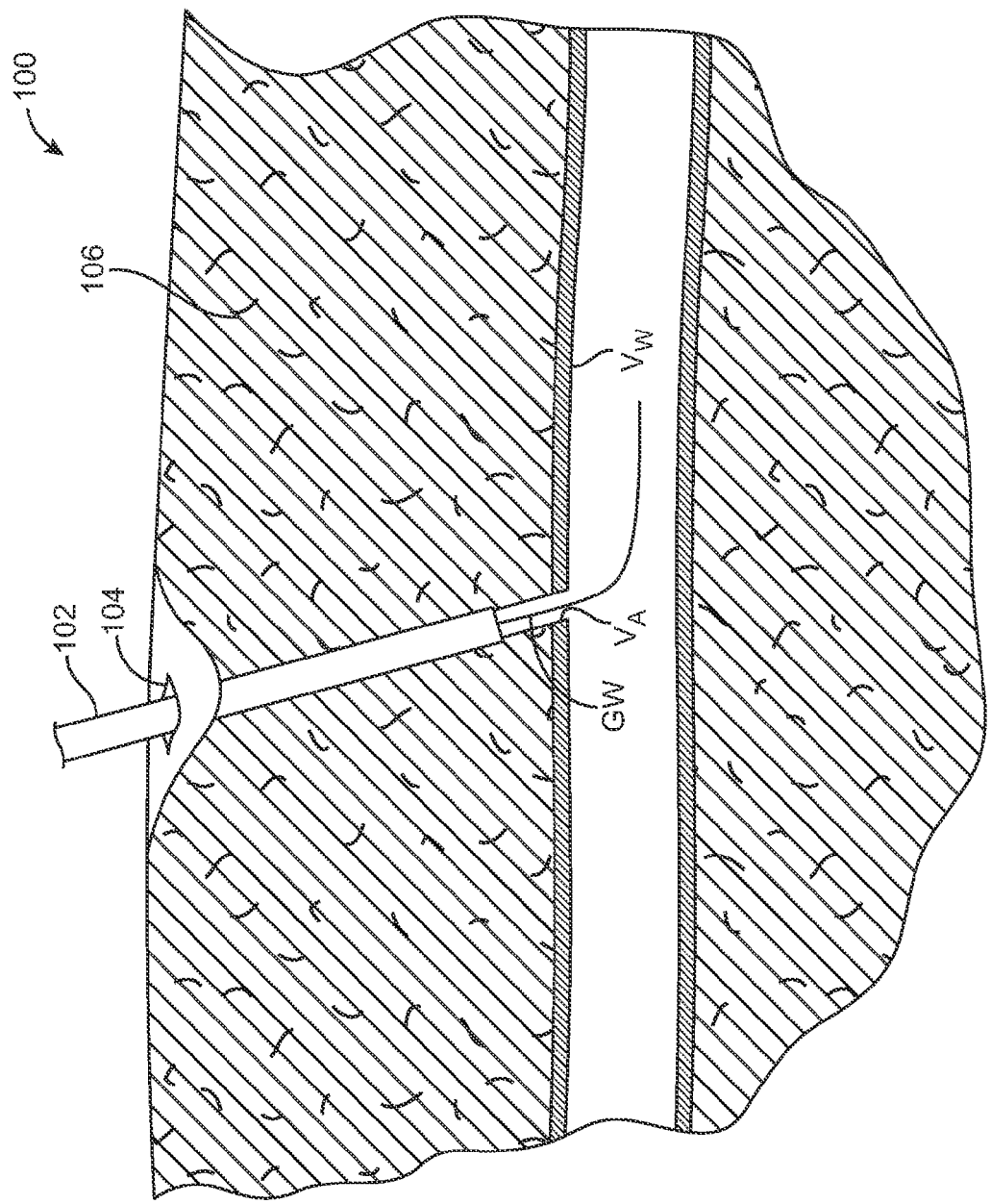
Figure 3:
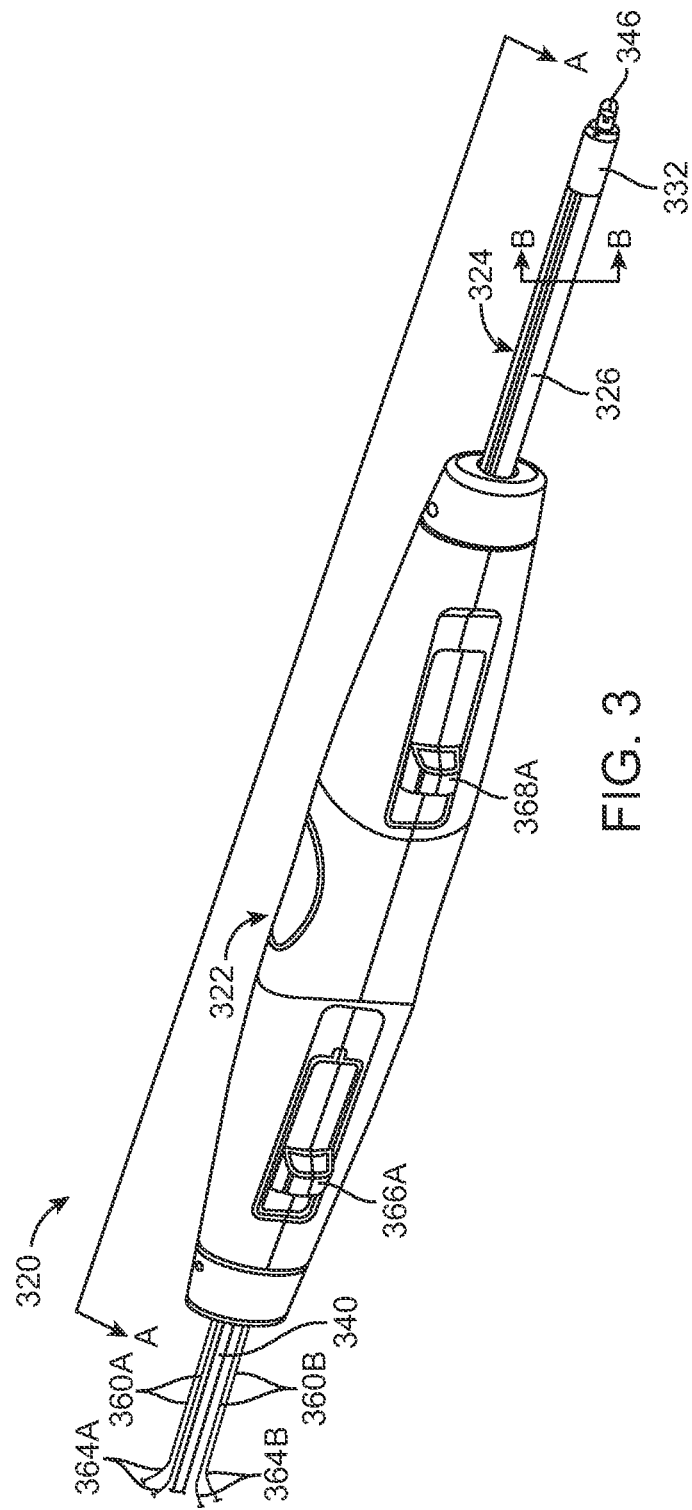
FIG. 3 is a perspective view of a suturing device according to an embodiment hereof for sealing or closing an arteriotomy, wherein the suturing device is in a delivery configuration in which the suture snags are in a retracted position and the needles and sutures are in a loaded position.
Figure 4C:
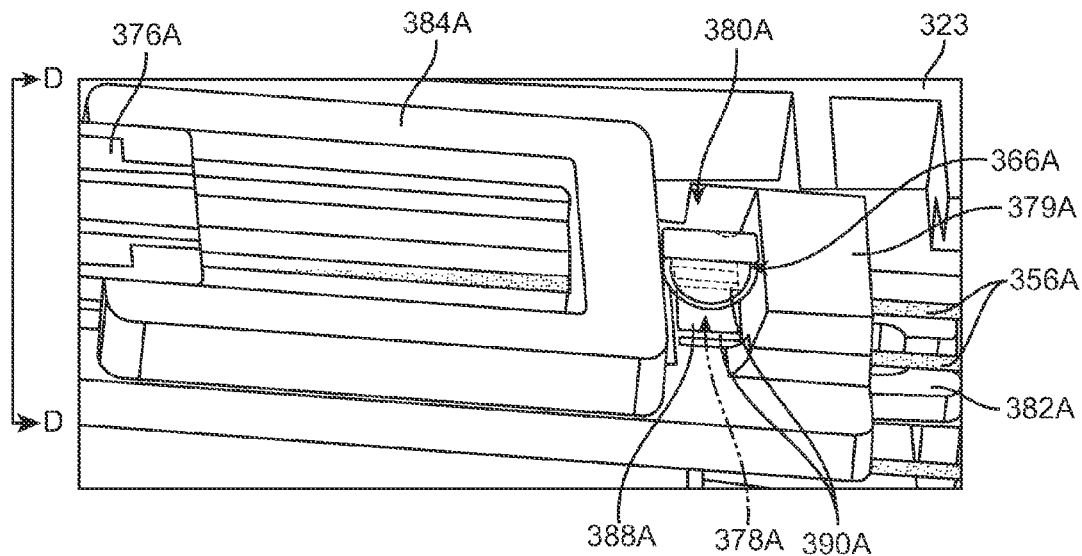
FIG. 4C is a cutaway view of a proximal portion of the handle of the suturing device of FIG. 3 exposing an actuation mechanism for deploying the needles and sutures.
Figure 4D:
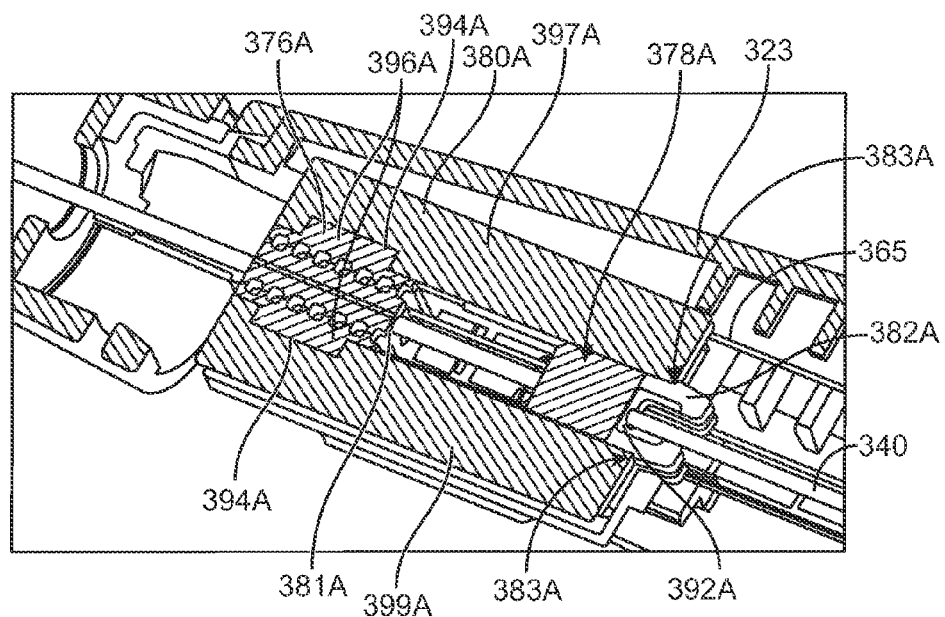
FIG. 4D is a sectional view taken along line D-D of FIG. 4C.
Figure 4E:
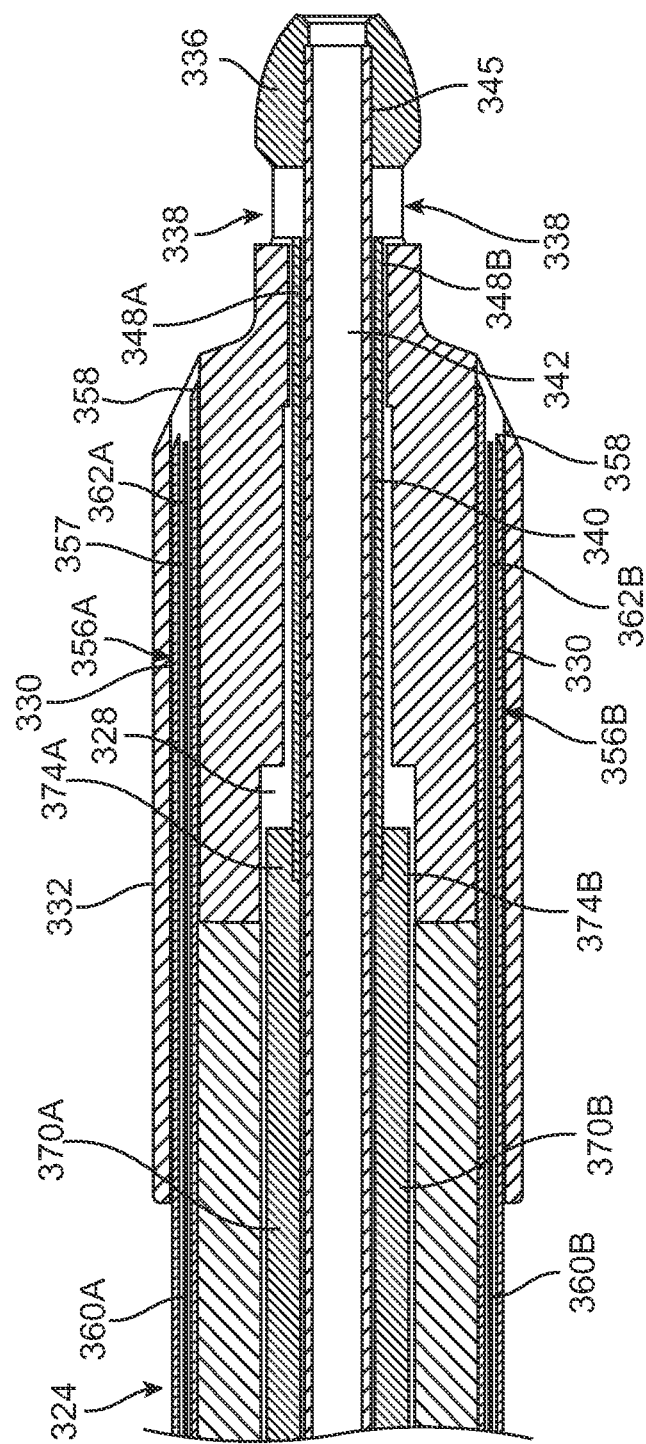
FIG. 4E is a sectional view of a distal portion of the suturing device of FIG. 3, wherein the suture snags are in the retracted position and the needles and sutures are in the loaded position.
Figure 4F:
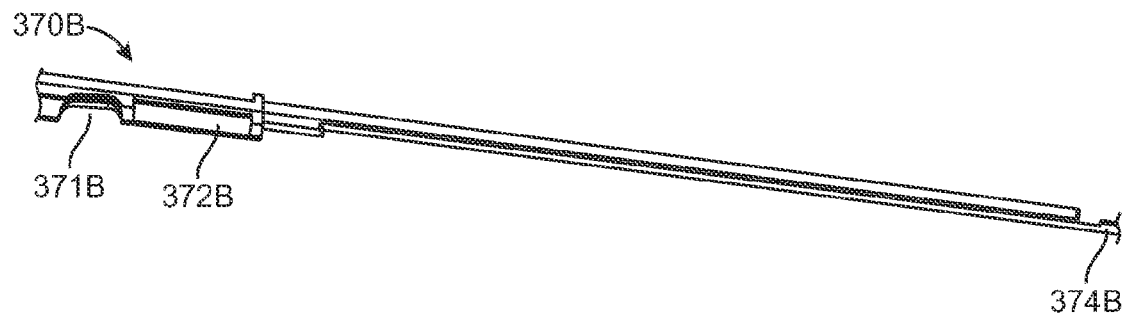
FIG. 4F is a perspective view of a transmission member of the suturing device of FIG. 3, wherein the transmission member is removed from the suturing device for illustrative purposes only.
Figure 4G:
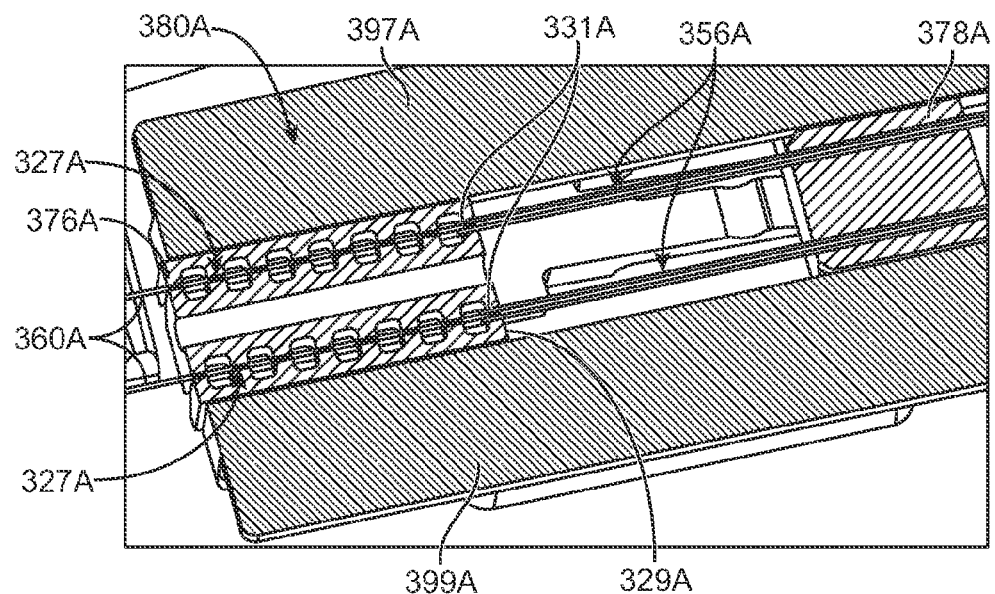
FIG. 4G is a sectional view taken along line G-G of FIG. 4D.

More particularly, as shown in the sectional view of FIG. 4E, two suture snags 348A, 348B in the collapsed or retracted position are located or housed in lumen 328 of elongated body 324 and are substantially parallel to a longitudinal axis of elongated body 324. Suture snags 348A, 348B are disposed within distal guiding component 332 during delivery of suturing device 320 so that they do not catch on the vessel walls of the vasculature during insertion and removal of the suturing device. Suture snags 348A, 348B are deployed by third and fourth actuators 368A, 368B, respectively, on handle 322 that interact with respective suture snag actuation mechanisms within handle 322 comprised of transmission members 370A, 370B. Suture snags 348A, 348B are coupled to the actuators via transmission members 370A, 370B, respectively. With additional reference to FIG. 4B which is a sectional view of handle 322 at actuators 368A, 368B and FIG. 4F which is a perspective view of transmission member 372B removed from the suturing device for illustrative purposes only, proximal ends 372A, 372B of transmission members 370A, 370B are located adjacent to actuators 368A, 368B, respectively, while distal ends 374A, 374B of transmission members 370A, 370B are attached or connected to suture snags 348A, 348B, respectively. In another embodiment hereof (not shown), transmission members 370A, 370B may be integrally formed with suture snags 348A, 348B.

Proximal ends 372A, 372B of transmission members 370A, 370B each include a recess or groove 371A, 371B, respectively, that form proximal surfaces 375A, 375B and distal surfaces 373A, 373B, respectively. When it is desired to deploy suture snag 348A, actuator 368A is slid forward or distally advanced such that a knob or boss 369A thereof slides or moves within recess 371A until it abuts against distal surface 373A and pushes or distally advances transmission member 370A, thereby also pushing or distally advancing suture snag 348A. Similarly, when it is desired to deploy suture snag 348B, actuator 368B is slid forward or distally advanced such that a knob or boss 369B thereof slides or moves within recess 371B until it abuts against distal surface 373B and pushes or distally advances transmission member 370B, thereby also pushing or distally advancing suture snag 348B. In the delivery configuration of the suturing device shown in FIGS. 4B and 4E, suture snags 348A, 348B are both in a retracted position with bosses 369A, 369B of actuators 368A, 368B, respectively, abutting against proximal surfaces 375A, 375B of recesses 371A, 371B of transmission members 370A, 370B, respectively. In addition, actuators 368A, 368B also abut against stops 359A, 359B, respectively, of a housing 323 of the handle 322 that project or protrude radially to limit proximal retraction of actuators 368A, 368B.

FIG. 4E also illustrates the loaded position of needles pairs 356A, 356B and suture pairs 360A, 360B. Each needle is a generally straight tubular shaft component or hypotube which defines a lumen 357 for slidingly receiving a suture and includes a distal end 358 configured to penetrate or pierce through the vessel wall. During delivery, a first suture of first suture pair 360A has a distal length disposed within a first needle of needle pair 356A and a second suture of first suture strand pair 360A has a distal length disposed within a second needle of needle pair 356A, wherein distal ends of the first and second sutures do not extend from the distal ends of their respective needles. Similarly, a first suture of second suture pair 360B has a distal length disposed within a first needle of needle pair 356B and a second suture of second suture pair 360B has a distal length disposed within a second needle of needle pair 356B, wherein distal ends of the first and second sutures do not extend from the distal ends of their respective needles. Each of the sutures of suture pairs 360A, 360B has a proximal length that extends proximally of handle 322 to be accessible to a clinician as described in more detail below. Outer shaft 326 and distal guiding component 332 collectively define or include a plurality of needle pathways or guides 330 for housing needle pairs 356A, 356B, which are slidingly disposed thereon or therein. With reference to the cross-sectional view of FIG. 3B, needle guides 330 may be formed via channels or grooves formed on an exterior surface of outer shaft 326 that mate with a plurality of lumens formed through distal guiding component 332. Alternatively, rather than channels or grooves formed on the outer surface thereof, outer shaft 326 may define individual lumens for housing each needle.

Needle pair 356A and suture pair 360A are deployed by actuator 366A that interact with a first needle and suture actuation mechanism within handle 322 comprised of a suture holder 376A, a needle holder 378A, and a carriage 380A. An identical second needle and suture actuation mechanism comprised of a needle holder 378B, a suture holder 376B, and a carriage 380B within handle 322 is utilized to deploy needle pair 356B and suture pair 360B via interaction with actuator 366B. In FIG. 4A, needle pairs 356A, 356B and suture pairs 360A, 360B are each in a loaded position, with suture pairs 360A, 360B disposed within their respective needle pair 356A, 356B. With reference to FIGS. 4A, 4C, and 4D, needle pair 356A is coupled to needle holder 378A and needle pair 356B is coupled to needle holder 378B. The needle pairs may be coupled to the respective needle holder via adhesive or other bonding mechanism. Similarly, when in the loaded position, suture pair 360A is coupled to a suture holder 376A which is formed of a resilient material such as silicone. As best shown in the sectional view of FIG. 4G, in the loaded position of the needle pairs and the suture pairs, proximal ends 331A of needle pair 356A are located within a portion of longitudinal slits 327A of suture holder 376A, adjacent to a distal end 329A of suture holder 376A, but at this stage of deployment the needle pair 365A does not extend through the suture holder. In order to couple each suture of suture pair 360A to suture holder 376A, each suture of suture pair 360A extends proximally from a respective proximal end 331A of needle pair 356A and extends through a respective longitudinal slit 327A of suture holder 376A. When suture holder 376A is distally advanced first with needle holder 378A during deployment of needle pair 365A and second decoupled from needle holder 378A during deployment of suture pair 360A, each suture of suture pair 360A is essentially squeezed or held via an interference fit within its respective slit 327A of suture holder 376A and therefore is distally advanced or carried by suture holder 376A. Suture pair 360B is similarly coupled to a suture holder 376B which is obscured from the views of FIGS. 4A, 4C, and 4D but may be seen in FIG. 8D.

In the delivery configuration of the suturing device, suture holder 376A and needle holder 378A are both coupled to a shuttle or carriage 380A of the actuation mechanism. As will be explained in more detail herein, actuator 366A pushes or distally advances carriage 380A in order to first extend or deploy needle pair 356A (via needle holder 378A coupled to carriage 380A) from the suturing device while carrying suture pair 360A loaded therein, and thereafter to extend or deploy suture pair 360A (via suture holder 376A which is also coupled to carriage 380A) relative to and distal of needle pair 356A. Similarly, in the delivery configuration of the suturing device, suture holder 376B and needle holder 378B are both coupled to a shuttle or carriage 380B, and actuator 366B pushes or distally advances carriage 380B in order to extend or deploy first needle pair 356B and then suture pair 360B. Needle holder 378A, suture holder 376A, carriage 380A, and actuator 366A are mirror images of needle holder 378B, suture holder 376B, carriage 380B, and actuator 366B, respectively, and as such, interactions of the actuation mechanism of needle holder 378A, suture holder 376A, and carriage 380A with actuator 366A is described herein.

More particularly, carriage 380A includes a first leg 397A, a second leg 399A, which extends substantially parallel but spaced apart from first leg 397A, and a distal bridge 379A, which extends between the distal ends of first and second legs 397A, 399A. Each leg 397A, 399A rides or slides along a track 365 of housing 323 of handle 322. Track 365 projects radially inward from the housing of the handle, and carriage 380A rides or slides along the track as it is distally advanced during extension of needle pair 356A and/or suture pair 360A as will be explained in more detail herein. Suture holder 376A is positioned within a proximal portion of carriage 380A, to be sandwiched between first and second legs 397A, 399A thereof, and is coupled to carriage 380A via integrally formed protrusions 396A of suture holder 376A which extend into corresponding recesses 394A of first and second legs 397A, 399A. Since suture holder 376A is coupled to carriage 380A, carriage 380A essentially pulls or carries suture holder 376A, and thus suture pair 360A attached thereto, forward when carriage 380A is distally advanced via actuator 366A. Suture holder 376A includes a longitudinal channel or groove 381A (see FIG. 4D) formed on an inner surface thereof for sliding or riding along inner shaft 340A.

Needle holder 378A includes a distal portion having claws or prongs 382A, a U-shaped proximal portion 384A, and an intermediate portion 388A extending therebetween. Intermediate portion 388A includes a pair of channels or grooves 390A formed on an outer surface thereof for receiving respective needles of needle pair 356A and also includes a channel or groove 392A (see FIG. 4D) formed on an inner surface thereof for sliding or riding along inner shaft 340A. In a delivery configuration of the suturing device, needle holder 378A is coupled to carriage 380A via mating or bearing surfaces 383A (see FIG. 4D). As a result of the interference fit between needle holder 378A and carriage 380A at bearing surfaces 383A, carriage 380A pushes or carries needle holder 378A, and thus needle pair 356A attached thereto, forward, i.e., in a distal direction, when carriage 380A is distally advanced via actuator 366A.

Figure 5:
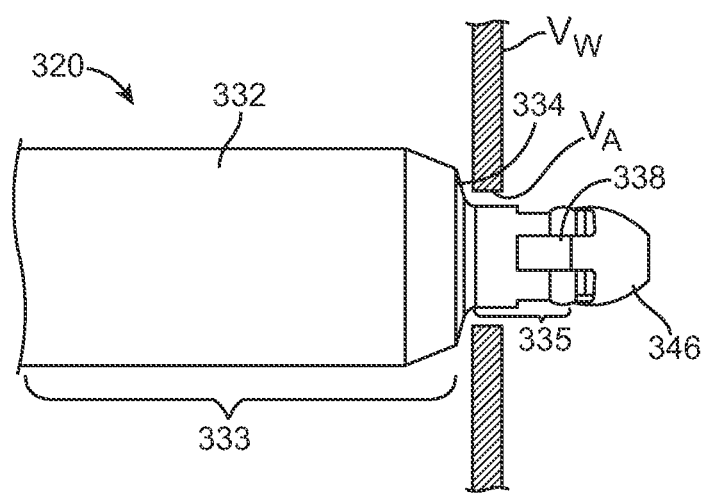
FIG. 5 is a side view illustration of a second step of the method of using the suturing device of FIG. 3 according to an embodiment hereof, wherein the suturing device is positioned through the arteriotomy.

Referring to FIG. 5, suturing device 320 is shown advanced to a position in which a distal portion thereof is positioned through a target arteriotomy $V_A$ such that distal tip 346 is disposed within a lumen of the vessel. Suturing device 320 is still in a delivery configuration, in which suture snags 348A, 348B are in a retracted position and needle pairs 356A, 356B and suture pairs 360A, 360B are in a loaded position as described above with respect to FIG. 4. Distal guiding component 332 includes a stepped or tapered region which creates an abutment surface 334. The outer diameter of a proximal portion 333 of distal guiding component 332, i.e., a portion which is proximal to abutment surface 334, is greater than the outer diameter of a distal portion 335 of distal guiding component 332, i.e., a portion which is distal to abutment surface 334. For example, the outer diameter of proximal portion 333 of distal guiding component 332 may be between 15 and 20 French while the outer diameter of distal portion 335 of distal guiding component 332 may be between 8 and 12 French. As shown in FIG. 5, distal portion 335 of distal guiding component 332 is sized to protrude through the arteriotomy $V_A$ and extend into the lumen of the vessel, while proximal portion 333 of distal guiding component 332 is sized to abut against the outer surface of the vessel wall $V_W$ and not protrude or extend through the arteriotomy $V_A$ and into the lumen of the vessel. When the user is advancing suturing device 320 to the arteriotomy $V_A$, a resistance to further advancement is felt when abutment surface 334 contacts the vessel wall, thereby notifying the user that the suturing device is in place within the arteriotomy $V_A$ as desired.

Figure 6:
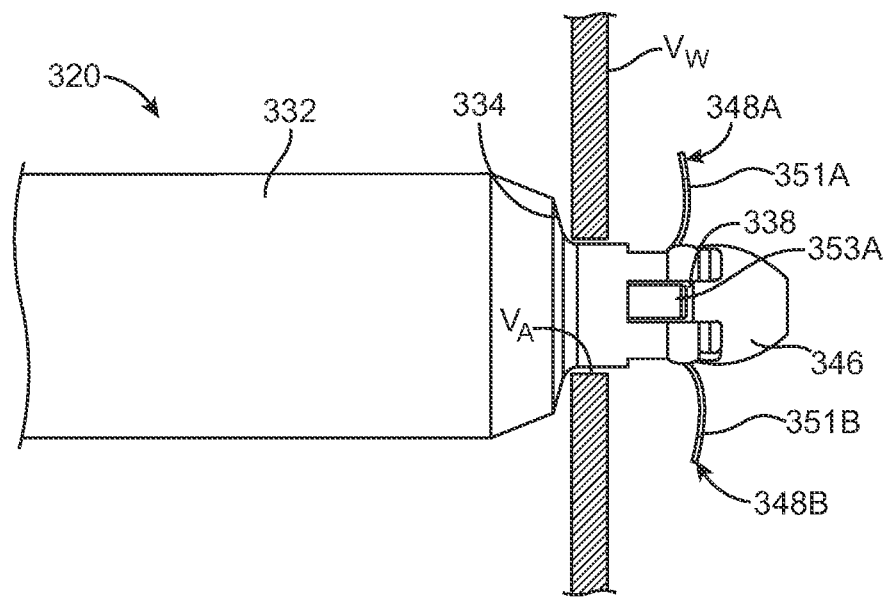
FIG. 6 is a side view illustration of a third step of the method of using the suturing device of FIG. 3 according to an embodiment hereof, wherein suture snags of the suturing device are deployed.

Once the distal portion of distal guiding component 332 is positioned through the arteriotomy $V_A$ of the vessel to reside within the lumen of the vessel, suture snags 348A, 348B are deployed against the vessel wall $V_W$ around the arteriotomy $V_A$ of the vessel as shown in FIG. 6. For illustrative purposes, suture snag 348A is shown in FIG. 6C in a deployed configuration removed from the suturing device. Suture snag 348B is identical to suture snag 348A and thus only the structure of suture snag 348A is described herein. Suture snag 348A includes two arms 350A, 352A which are disposed at an angle of approximately 90 degrees relative to each other. "Approximately" as utilized herein includes a range of plus or minus ten degrees. The proximal ends of arms 350A, 352A are joined via a connector 354A. Distal ends 374A, 374B of transmission members 370A, 370B may fit within a space or gap 337 between arms 350A, 352A to thereby couple transmission members 370A, 370B to suture snag 348A, although other mechanisms for coupling the transmission members and the suture snags may be used. When suturing device 320 is being delivered, arms 350A, 352A are generally straight. However, in the deployed configuration shown in FIG. 6C, distal arm portions 351A, 353A of each arm 350A, 352A, respectively, curve or extend radially outward from a longitudinal axis of the suturing device because at least distal arm portions 351A, 353A are formed from a resilient material having a mechanical memory. Mechanical memory may be imparted by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Distal arm portions 351A, 353A of suture snag 348A each include a thru-hole or aperture 355 there through. Aperture 355 is generally circular or elliptical but includes two radial extensions 339 of the aperture or hole that function to catch or grip the ends of the suture as will be described in more detail herein. As will be shown in an additional embodiment described herein, if a single needle pair and a single suture snag are included on a suturing device to deploy a single suture pair, the distal arm portions of the suture snag are circumferentially spaced at approximately 180 degrees from each other. However, when two suture snags are included on a suturing device such as suturing device 320, the distal arm portions of each suture snag are circumferentially spaced approximately 90 degrees from each other.

Figure 6A:
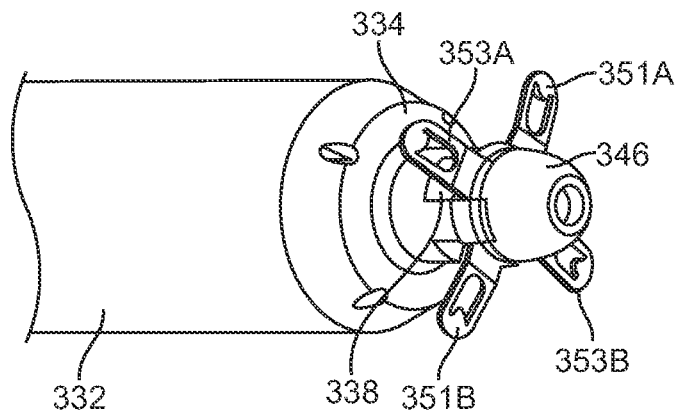
FIG. 6A is a perspective view of a distal portion of the suturing device of FIG. 3, wherein the suture snags of the suturing device are deployed.
Figure 6B:
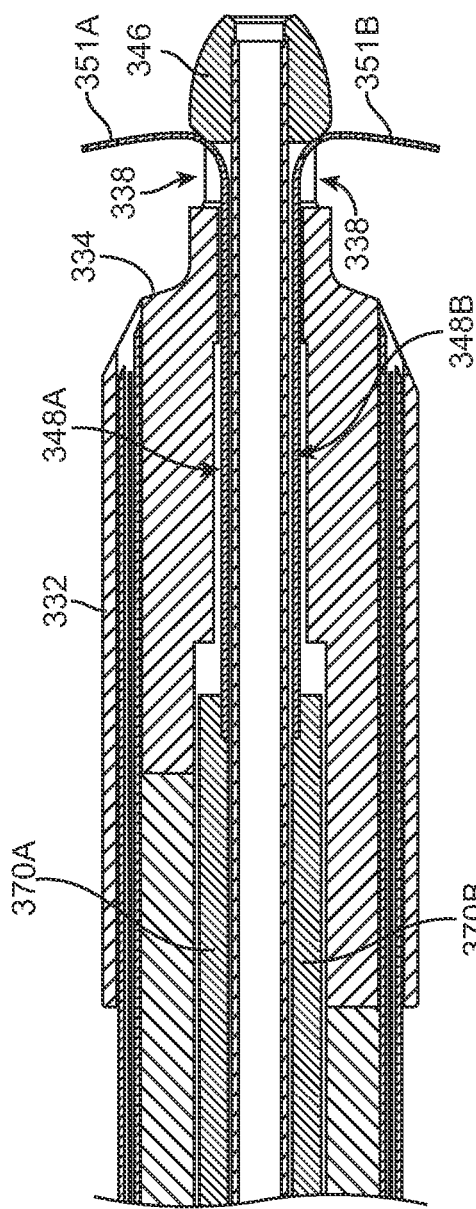
FIG. 6B is a sectional view of a distal portion of the suturing device of FIG. 3, wherein the suture snags of the suturing device are deployed.
Figure 6C:
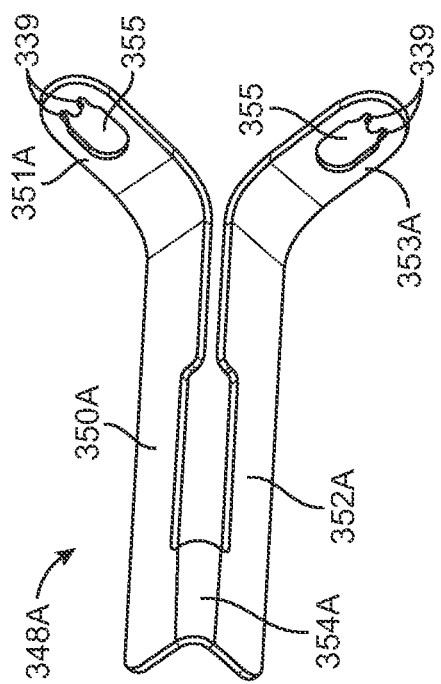
FIG. 6C is a perspective view of a suture snag of FIG. 3 removed from the suturing device for illustrative purposes only, wherein the suture snag is in a deployed position.
Figure 6D:
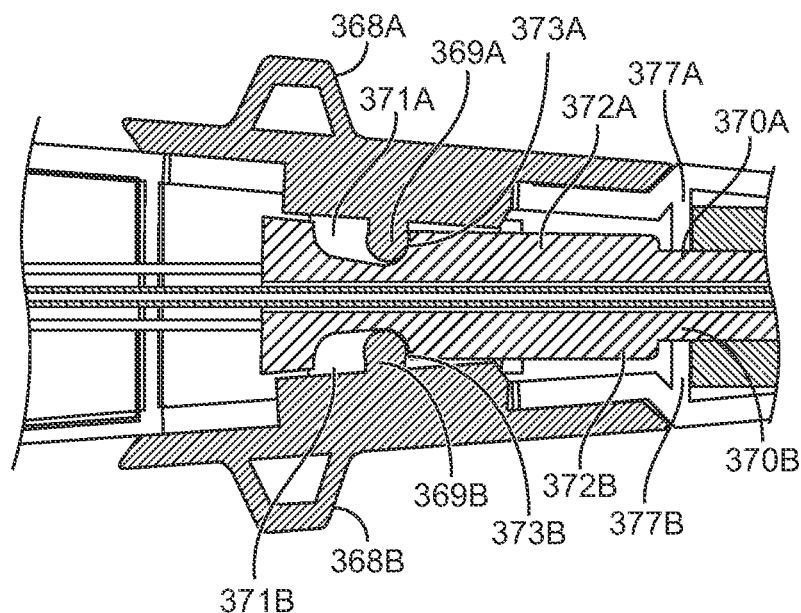
FIG. 6D is a sectional view of a distal portion of the handle of the suturing device of FIG. 3 with the actuation mechanisms for deploying the suture snags shown in a deployed position.
Figure 6E:
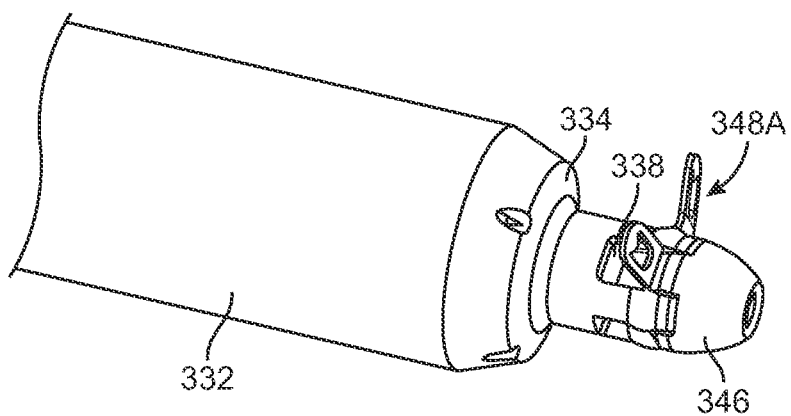
FIG. 6E is a perspective view of a distal portion of the suturing device of FIG. 3, wherein only one suture snag of the suturing device is deployed.

Distal guiding component 332 includes four passageways or openings 338 formed at a distalmost end thereof which allow the distal arm portions of the two suture snags 348A, 348B to alternate between the retracted position during delivery in which each suture snag 326 is disposed within and is substantially parallel to elongated body 324, as shown and described above with respect to FIGS. 4 and 5, and a second deployed position in which the distal arm portions of each suture snag 348A, 348B extend radially outward from openings 338 away from the elongated body, as shown in FIGS. 6, 6A, and 6B. With reference to FIG. 6D which is a sectional view of handle 322 at actuators 368A, 368B, when it is desired to deploy suture snag 348A, actuator 368A is distally advanced such that boss 369A thereof abuts against distal surface 373A and pushes or distally advances transmission member 370A, thereby also pushing or distally advancing distal arm portions 351A, 353A of suture snag 348A out of two of the four openings 338 of distal guiding component 332. Similarly, when it is desired to deploy suture snag 348B, actuator 368B is distally advanced such that boss 369B thereof abuts against distal surface 373B and pushes or distally advances transmission member 370B, thereby also pushing or distally advancing distal arm portions 351B, 353B of suture snag 348B out of the other two of the four openings 338 of distal guiding component 332. It will be apparent to one of ordinary skill in the art that suture snags 348A, 348B may be deployed simultaneously or independently. FIGS. 6A and 6B illustrate both suture snags 348A, 348B deployed, while FIG. 6E illustrates only suture snag 348A deployed. When each suture snag 348A, 348B is distally advanced via actuator 368A, 368B, respectively, distal arm portions 351A, 353A, 351B, 353B extend out of openings 338 formed at a distalmost end of distal guiding component 332. The mechanical memory of each suture snag causes the distal arm portions 351A, 353A, 351B, 353B to assume their deployed configurations and radially extend. When deployed, distal arm portions 351A, 353A, 351B, 353B of suture snags 348A, 348B, respectively, lie adjacent to or against an inside surface of the vessel wall $V_W$ with respective apertures 355 thereof positioned radially outward of the arteriotomy $V_A$. FIG. 6D illustrates actuators 368A, 368B when both suture snags 348A, 348B are in a deployed position with bosses 369A, 369B of actuators 368A, 368B, respectively, abutting against distal surfaces 373A, 373B of recesses 371A, 371B of transmission members 370A, 370B, respectively. Proximal ends 372A, 372B of transmission members 370A, 370B, respectively, abut against stops 377A, 377B, respectively, of housing 323 of handle 322 which project radially inward to limit distal advancement of actuators 368A, 368B.

Figure 7:
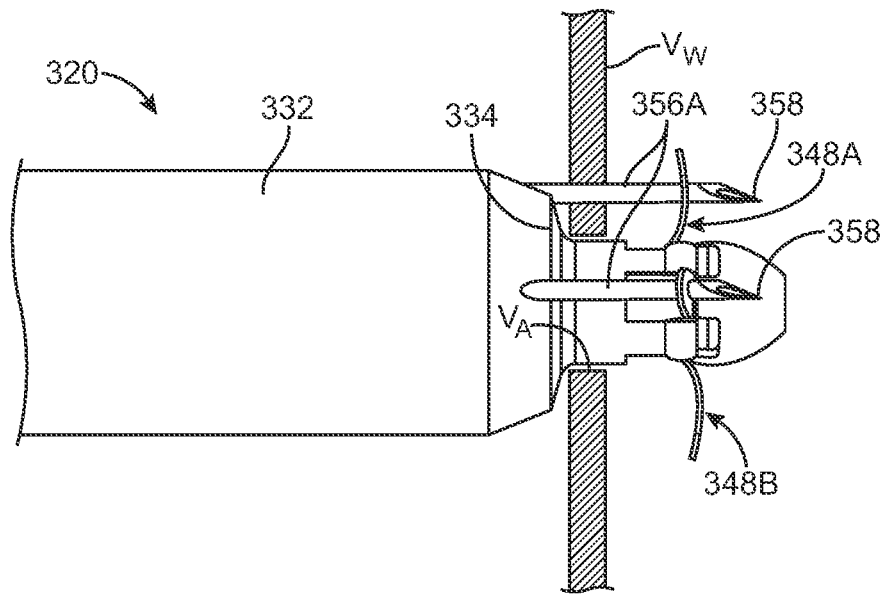
FIG. 7 is a side view illustration of a fourth step of the method of using the suturing device of FIG. 3 according to an embodiment hereof, wherein a pair of needles with sutures therein are deployed to extend through the vessel wall adjacent to the arteriotomy.
Figure 7A:
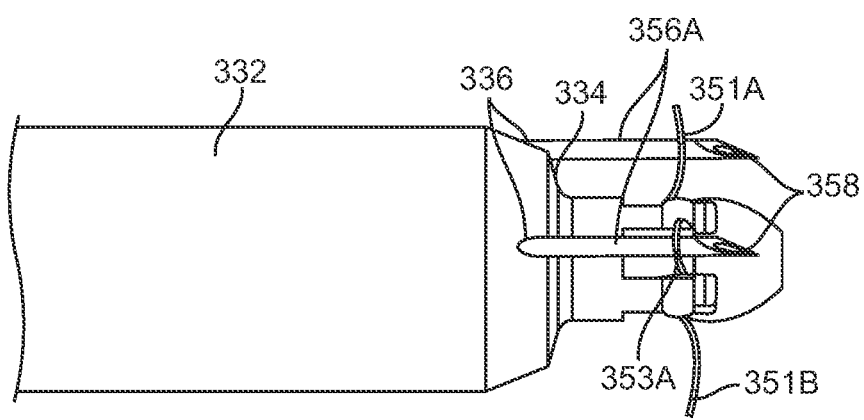
FIG. 7A is a perspective view of a distal portion of the suturing device of FIG. 3, wherein the needles with the sutures therein are deployed.

After suture snags 348A, 348B are deployed, needle pair 356A and suture pair 360A are distally advanced until the respective actuation mechanism has reached a needle deployment position wherein the needles pierce through the vessel wall $V_W$ at points that are radially outward of the arteriotomy $V_A$ as shown in FIG. 7. In one embodiment, as shown in FIGS. 7 and 7A, only needle pair 356A is first extended into a lumen of a vessel. Extending only one needle pair into the vessel at a time provides access to relatively smaller vessels. However, it will be understood that both needle pairs may alternatively be extended or deployed into the vessel wall at the same time. With additional reference to the perspective view of FIG. 7A, needle pair 356A is distally advanced out of distal ports 336 of distal guiding component 332 and is distally advanced through tissue around the arteriotomy of a vessel until distal ends 358 of the needles extend through apertures 355 of deployed suture snags 348A, 348B. Accordingly, in situ, needle pair 356A creates incisions or pathways within tissue around the arteriotomy during deployment. Although not visible in the views of FIGS. 7 and 7A, suture pair 360A extending within and carried with needle pair 356A is similarly distally advanced concurrently with needle pair 356A. Notably, since needle pair 356A is distally deployed out of the relatively larger proximal portion of distal guiding component 332, the needles extend straight out of ports 336 to pierce through the vessel wall $V_W$ and do not need to bend or curve. As such, the amount of force or energy required to extend the needles is minimized. Further, since no bending is required, the needles may be formed from stainless steel for improved pushability. In an embodiment, the outer diameter of the needles ranges between 0.015 and 0.025 inches, but needles with other diameters may be used herewith.

Figure 7B:
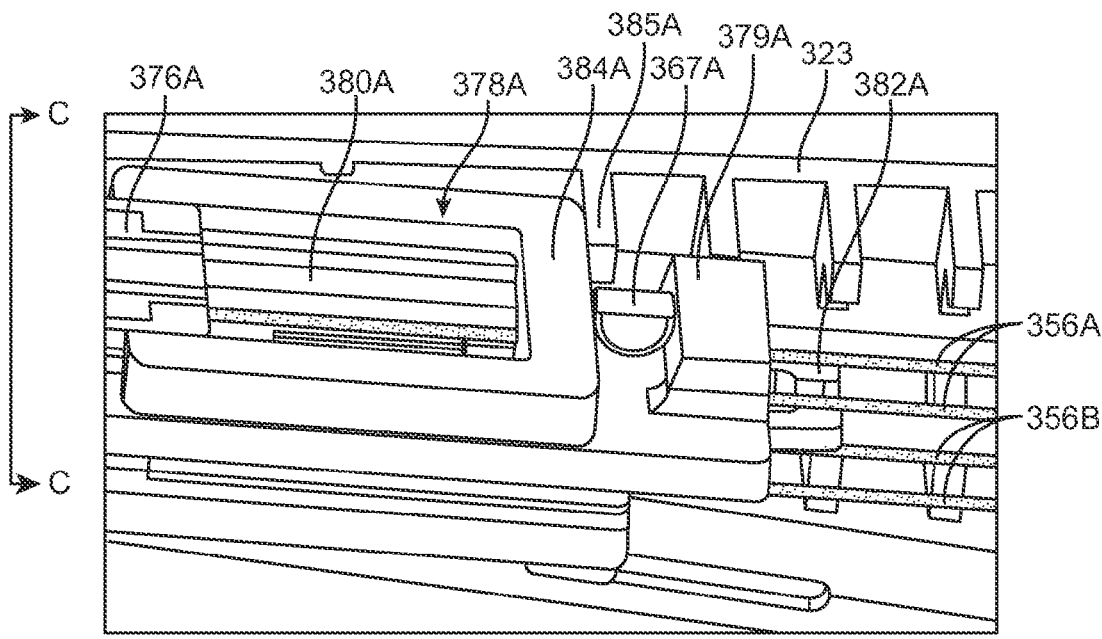
FIG. 7B is a cutaway view of a distal portion of the handle of the suturing device of FIG. 3 exposing actuation mechanisms for deploying the needles and sutures with the top actuation mechanism shown in a needle deployment position.

In order to extend needle pair 356A and suture pair 360A to the position shown in FIG. 7, actuator 366A on handle 322 is distally advanced until the actuation mechanism associated therewith reaches a needle deployment position. With reference to FIG. 7B which is a cutaway view of handle 322 at actuator 366A, a knob or boss 367A (shown in phantom) of actuator 366A is positioned proximal to and abuts against distal bridge 379A of carriage 380A. When actuator 366A is pushed forward or distally advanced, boss 367A pushes or distally advances carriage 380A, thereby also distally advancing in unison both suture holder 376A (and suture pair 360A coupled thereto) and needle holder 378A (and needle pair 356A coupled thereto). Since suture holder 376A is coupled to carriage 380A via protrusions 396A which mate with corresponding recesses 394A as described above, carriage 380A pulls or carries suture holder 376A, and thus suture pair 360A attached thereto, forward when carriage 380A is distally advanced via actuator 366A. In addition, since needle holder 378A is coupled to carriage 380A via an interference fit between bearing surfaces 383A as described above, carriage 380A pushes or carries needle holder 378A, and thus needle pair 356A attached thereto, forward when carriage 380A is distally advanced via actuator 366A. Needle holder 378A is carried by or moves concurrently with carriage 380A until U-shaped proximal portion 384A of the needle holder abuts against a stop 385A of housing 323 of handle 322, such that the needle deployment position has been reached as shown in FIG. 7B. Needle holder 378A, as well as needle pair 356A attached thereto, cannot be distally advanced after U-shaped proximal portion 384A of the needle holder abuts against stop 385A. As such, at this point in the method of use, needle pair 356A is in an extended deployed position while suture pair 360A may be considered to be in a partially extended position or as remaining in a loaded position within needle pair 356A.

Figure 7C:
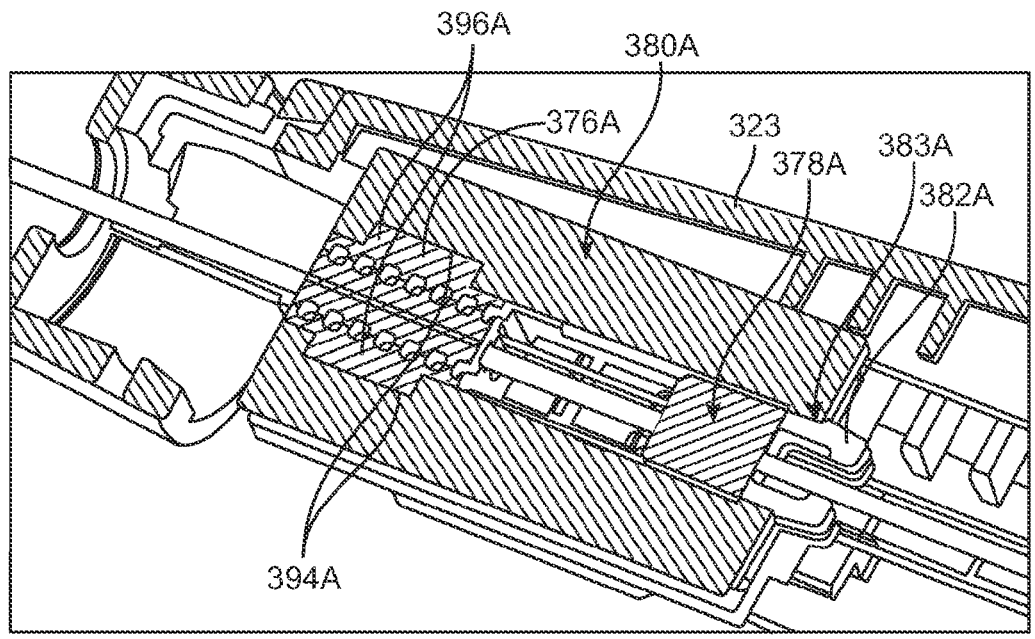
FIG. 7C is a sectional view taken along line C-C of FIG. 7B.
Figure 8:
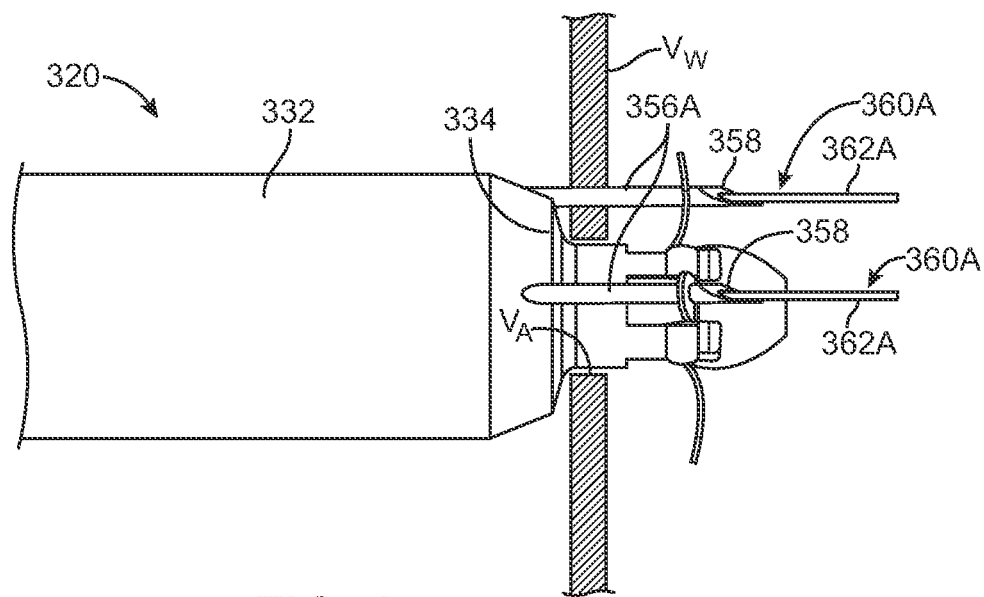
FIG. 8 is a side view illustration of a fifth step of the method of using the suturing device of FIG. 3 according to an embodiment hereof, wherein the sutures are deployed to extend beyond the distal ends of the needles.
Figure 8A:
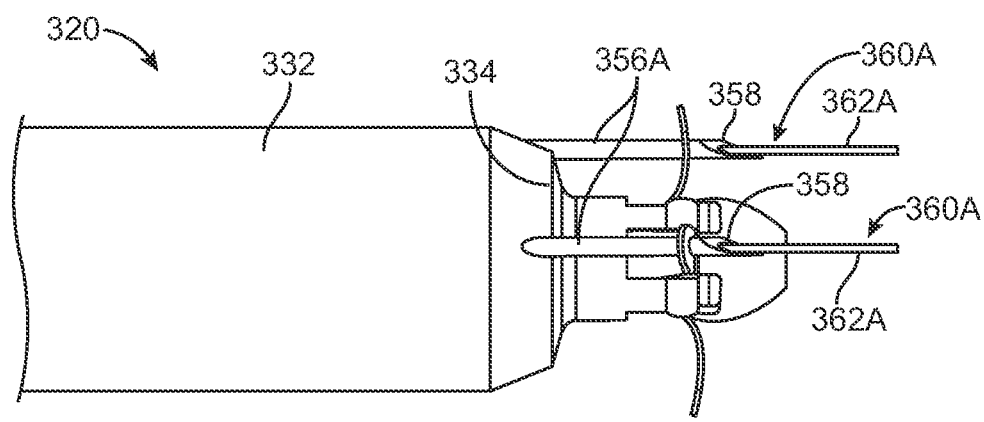
FIG. 8A is a perspective view of a distal portion of the suturing device of FIG. 3, wherein the sutures of the suturing device are deployed to extend beyond the distal ends of the needles.
Figure 8B:
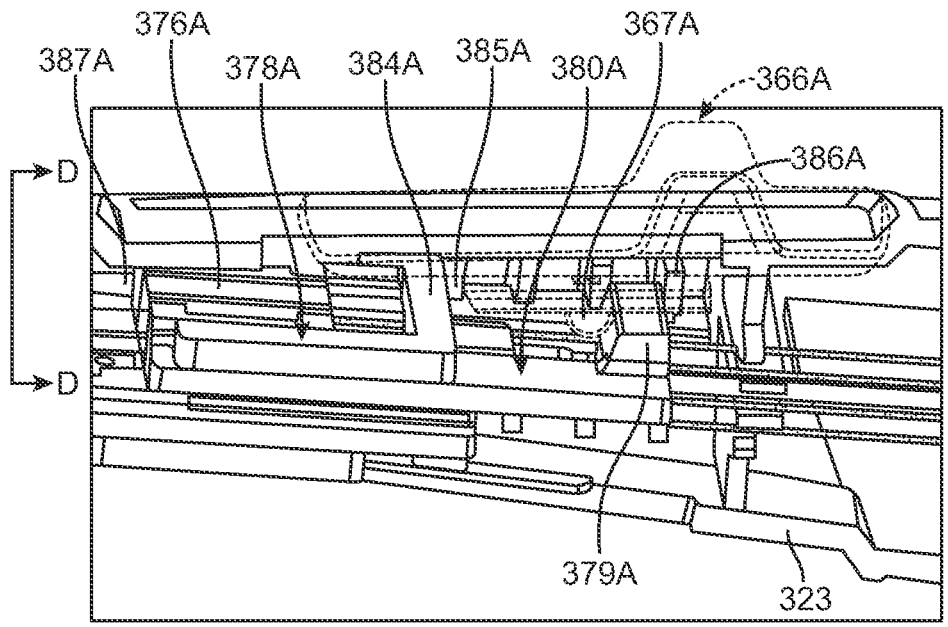
FIG. 8B is a cutaway view of a proximal portion of the handle of the suturing device of FIG. 3 exposing actuation mechanisms for deploying the needles and sutures with the top actuation mechanism shown in a suture deployment position.
Figure 8C:
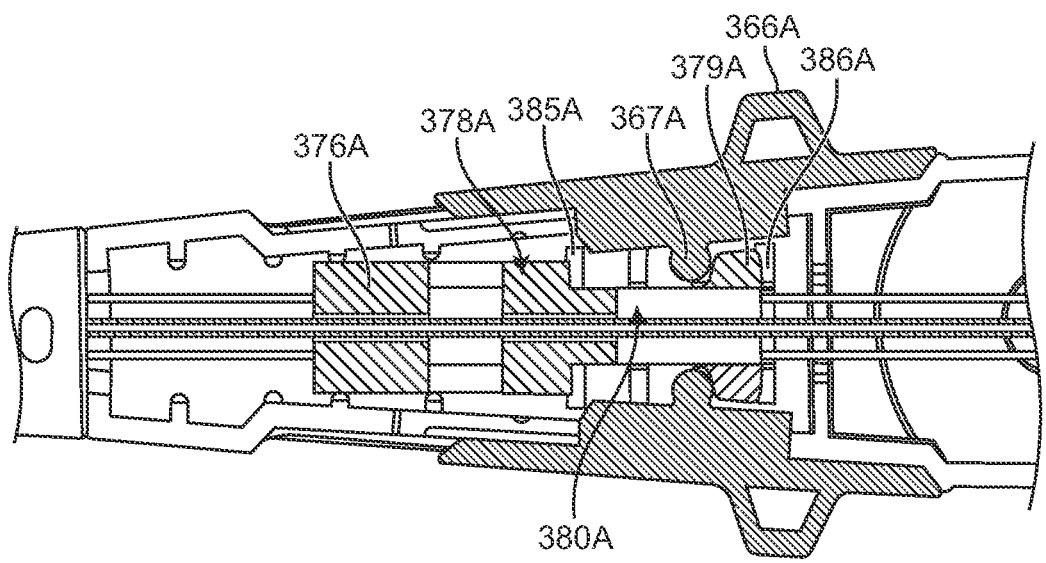
FIG. 8C is a sectional view of a proximal portion of the handle of the suturing device of FIG. 3, wherein the actuation mechanisms for extending the needles and sutures are both shown in a fully extended suture deployment position.
Figure 8D:
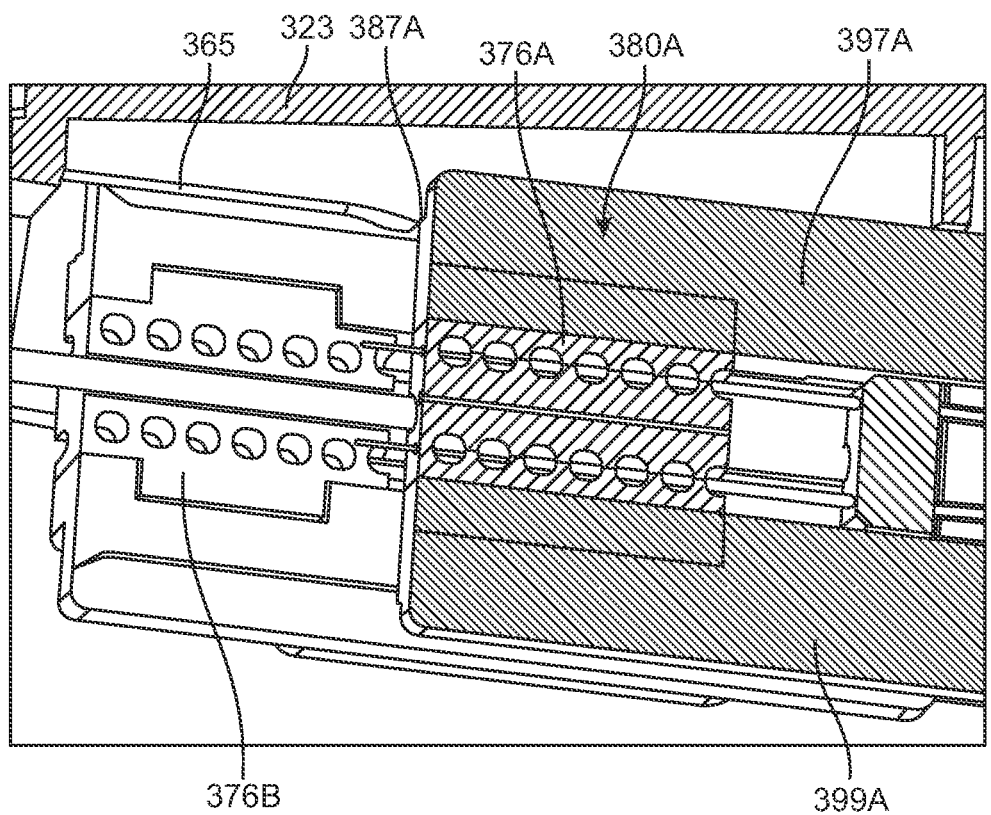
FIG. 8D is a sectional view taken along line D-D of FIG. 8B.

First ends 362A of suture pair 360A are then deployed out of or beyond distal ends 358 of needle pair 356A as shown in FIGS. 8 and 8A. In order to extend or deploy suture pair 360A out of needle pair 356A, actuator 366A on handle 322 is further distally advanced until the actuation mechanism associated therewith reaches a suture deployment position. With reference to FIGS. 8B and 8C which are cutaway and sectional views, respectively, of handle 322 at actuator 366A, further distal advancement of actuator 366A (shown in phantom in FIG. 8B) results in carriage 380A disengaging or decoupling from needle holder 378A so that carriage 380A and suture holder 376A may be further distally advanced. As previously explained, needle holder 378A is prevented from further distal movement because U-shaped proximal portion 384A of the needle holder abuts against stop 385A of housing 323 of handle 322. With additional reference back to the sectional view of FIG. 7C, as carriage 380A is further distally advanced via actuator 366A, carriage 380A overcomes the interference fit between bearing surfaces 383A and thereby squeezes or compresses distal prongs 382A of needle holder 378A to allow the carriage to slidingly advance over the needle holder. Carriage 380A, as well as suture holder 376A and suture pair 360A coupled thereto, are distally advanced via actuator 366A until distal bridge 379A of carriage 380A abuts against a stop 386A of housing 323 of handle 322 such that the suture deployment position has been reached. As such, suture pair 360A is distally advanced relative to needle pair 356A by continued movement of actuator 366A. Although the distal advancement of actuator 366A is described in two sequential method steps within FIGS. 7 and 8, it will be understood by those of ordinary skill in the art that such steps are performed by a single user action, i.e., distal advancement of actuator 366A.

Carriage 380A rides or slides along track 365 of housing 323 of handle 322 as carriage 380A is distally advanced towards stop 386A. Track 365 includes a stop 387A that projects radially inward from housing 323 of handle 322. When carriage 380A is distally advanced to the point that distal bridge 379A abuts against stop 386A, a proximalmost end or surface of carriage 380A passes over stop 387A such that the proximalmost end or surface of carriage 380A is located distal to stop 387A as shown in the sectional view of FIG. 8D. Carriage 380A may bow or arch as it passes or rides over stop 387A, and then snap back to its flat or planar shape when the proximalmost end or surface of carriage 380A is located distal to stop 387A. Stop 387A prevents retraction of carriage 380A and suture holder 376A coupled thereto, thereby locking the fully extended deployed position of suture pair 360A.

Figure 9:
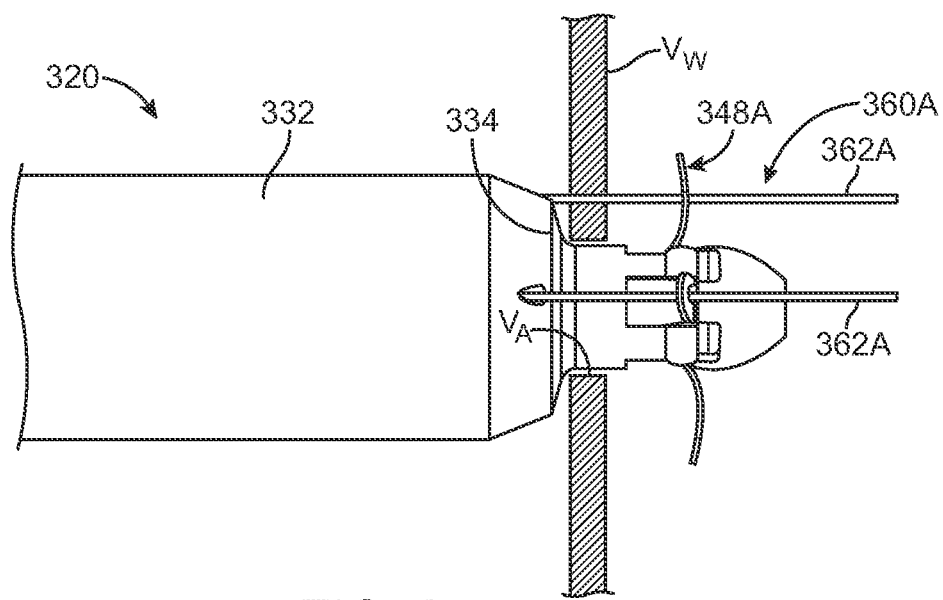
FIG. 9 is a side view illustration of a sixth step of the method of using the suturing device of FIG. 3 according to an embodiment hereof, wherein the pair of needles have been proximally retracted leaving a pair of sutures deployed within a corresponding pair of suture snags.
Figure 9A:
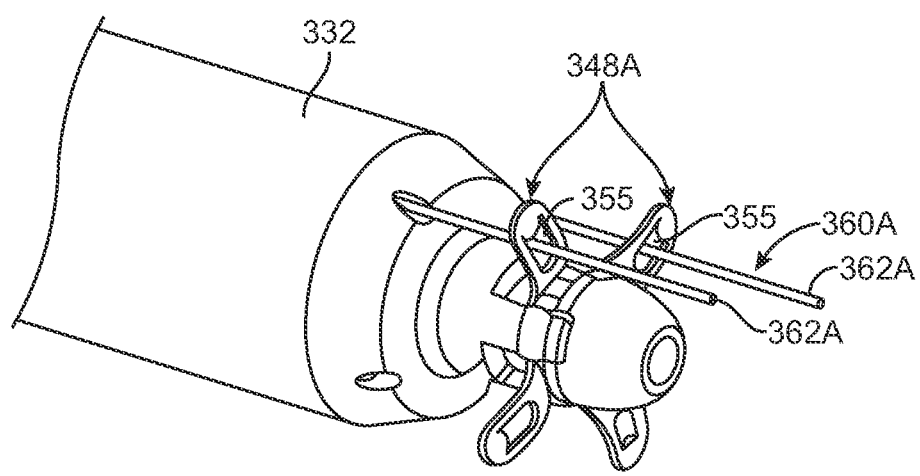
FIG. 9A is a perspective view of a distal portion of the suturing device of FIG. 3, wherein the pair of needles shown in FIG. 8A have been proximally retracted leaving a pair of sutures deployed within a corresponding pair of suture snags.
Figure 9B:
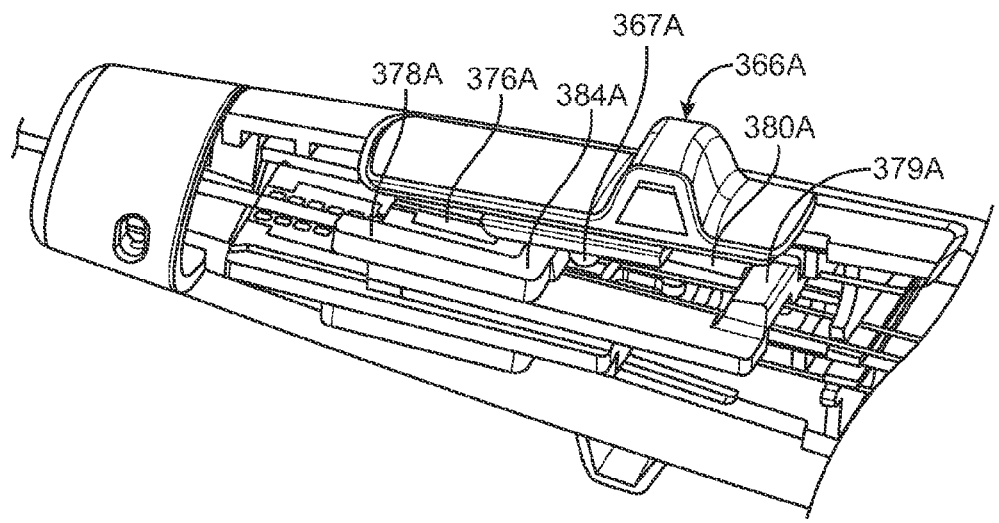
FIG. 9B is a cutaway view of a proximal portion of the handle of the suturing device of FIG. 3 exposing actuation mechanisms for deploying the needles and sutures with the actuation mechanisms shown in needle retraction positions with the sutures deployed.
Figure 9C:
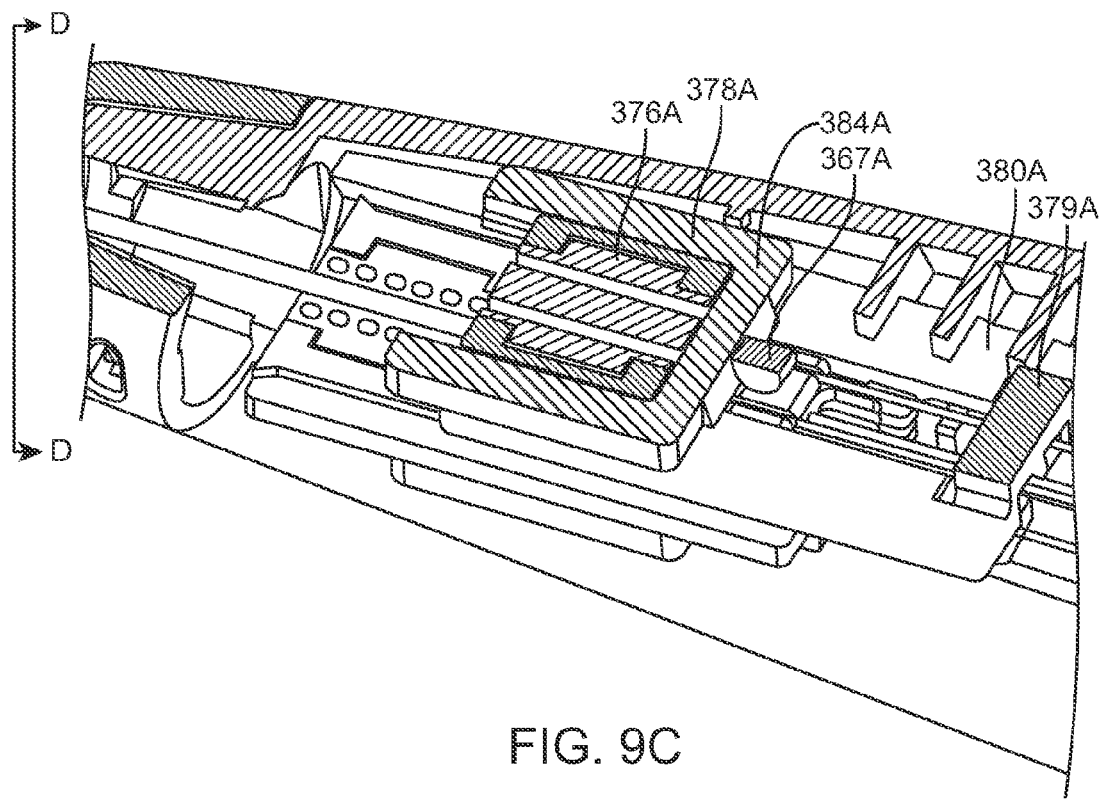
FIG. 9C is a sectional view of a proximal portion of the handle of the suturing device of FIG. 3 exposing actuation mechanisms for deploying the needles and sutures the actuation mechanisms are shown having retracted the needles while the sutures remain extended.

After distal portions of suture pair 360A are extended or deployed beyond needle pair 356A, needle pair 356A is retracted as shown in FIGS. 9 and 9A, thereby leaving only the suture ends extending through the vessel wall and through apertures 355 of deployed suture snag 348A. With additional reference to the cutaway and sectional views of FIGS. 9B and 9C, respectively, actuator 366A is proximally refracted until boss 367A thereof abuts against U-shaped proximal portion 384A of needle holder 378A and then actuator 366A pushes or proximally retracts the needle holder, thereby also proximally retracting needle pair 356A. Carriage 380A and suture pair 360A cannot be retracted since they are locked in their extended positions due to stop 387A, as described above, and needle holder 378A is free to move independently from and relative to carriage 380A since it was previously decoupled therefrom. Needle holder 378A and needle pair 356A attached thereto are proximally retracted until U-shaped proximal portion 384A of the needle holder abuts against suture holder 376A, such that the actuation mechanism may be considered to have reached a needle retraction position as shown in FIGS. 9B and 9C. Once needle holder 378A is in its needle retraction position, distal tips 358 of needle pair 356A are retracted back into distal guiding component 332.

Figure 9D:
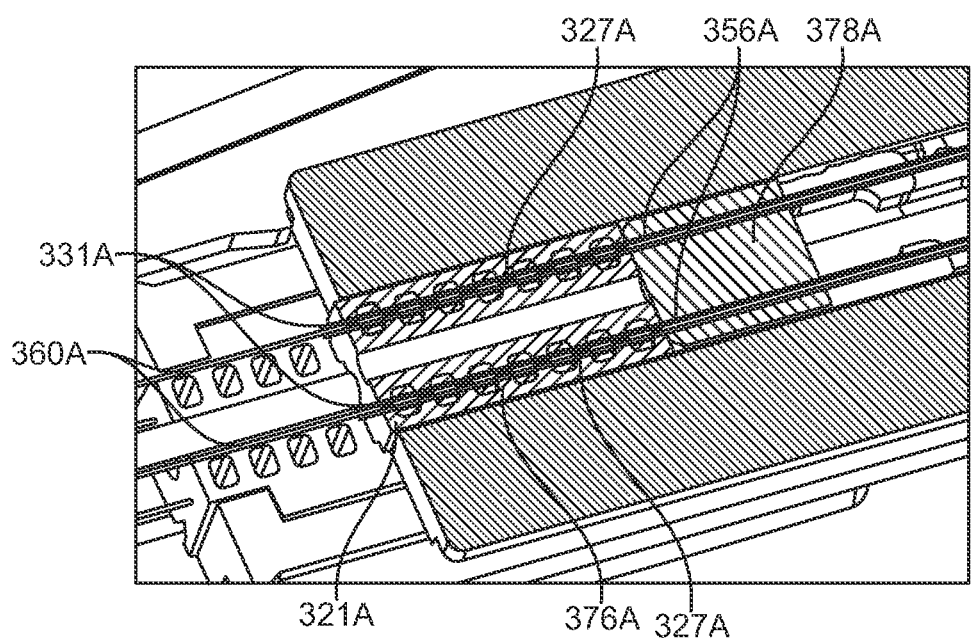
FIG. 9D is a sectional view taken along line D-D of FIG. 9C.

In addition, when needle pair 356A is in the retracted position shown in FIGS. 9, 9A, 9B, and 9C, needle pair 356A extends through longitudinal slits 327A of suture holder 376A such that proximal ends 331A of needle pair 356A are located proximal to a proximal end 321A of suture holder 376A as best shown in the sectional view of FIG. 9D to envelop or surround suture pair 360A such that suture pair 360A is slidingly positioned through needle pair 356A, and therefore is no longer coupled to suture holder 376A. Stated another way, since suture pair 360A is slidably disposed within needle pair 356A for the entire length of suture holder 376A, suture pair 360A no longer contacts the suture holder and therefore is no longer squeezed or held via an interference fit within longitudinal slits 327A of suture holder 376A. Since needle pair 356A extends through the length of suture holder 376A, suture pair 360A disengages from or decouples from suture holder 376A.

Figure 10:
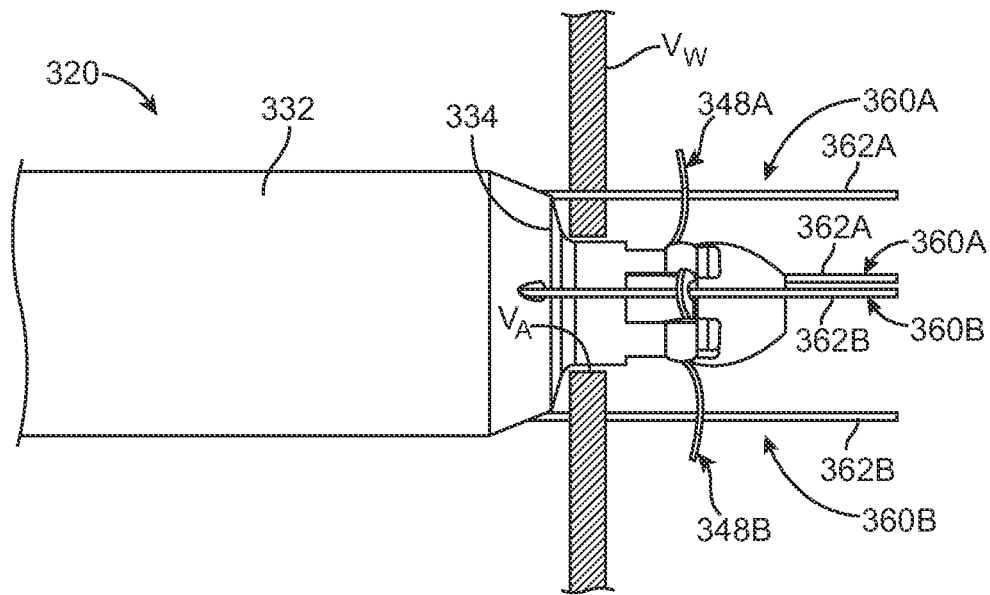
FIG. 10 is a side view illustration of a seventh step of the method of using the suturing device of FIG. 3 according to an embodiment hereof, wherein two sutures are shown extending into the arteriotomy.

As previously mentioned with respect to FIG. 7, it may be desirable to extend only a single needle pair at a time into a lumen of a vessel if the vessel is of a relatively smaller size. If only a single needle pair and corresponding suture pair has been deployed into the lumen of the vessel, the remaining needle pair 368B and first ends 362B of suture pair 360B are subsequently extended into the lumen of the vessel via actuator 366B as shown in FIG. 10 by following the method steps described above with respect to actuator 366A. Alternatively, suture pair 360B may have been extended into the lumen of the vessel via actuator 366B before or concurrently with suture pair 360A.

Figure 11:
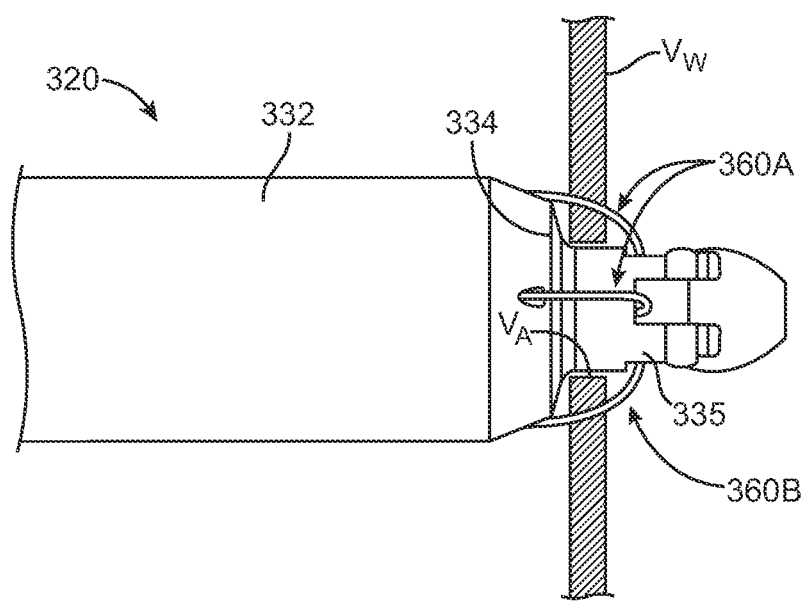
FIG. 11 is a side view illustration of an eighth step of the method of using the suturing device of FIG. 3 according to an embodiment hereof, wherein the suture snags of the suturing device are proximally retracted, thereby capturing the suture ends.
Figure 11A:
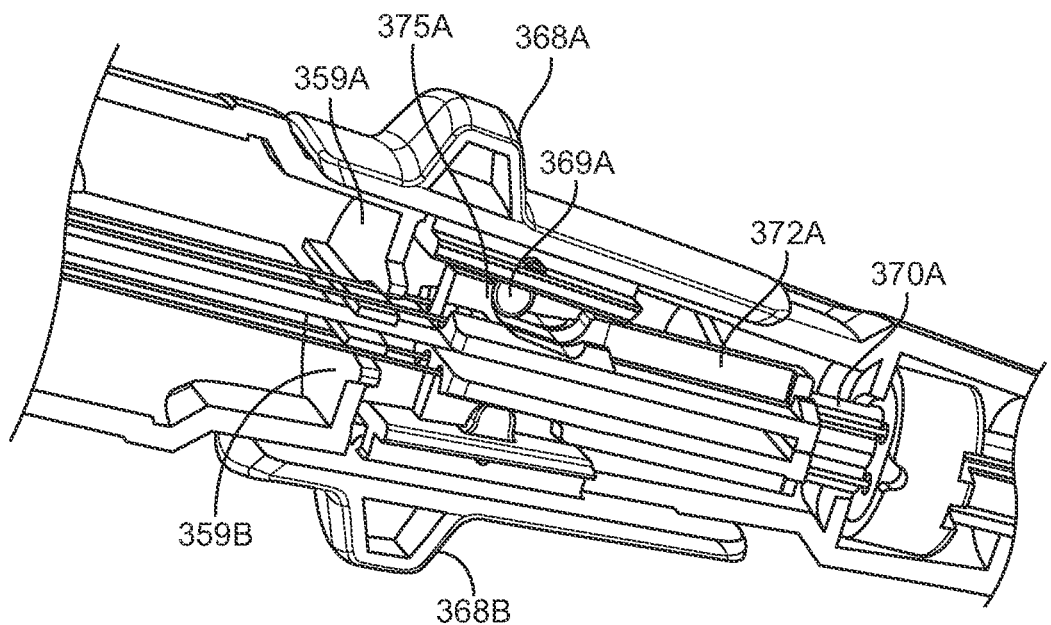
FIG. 11A is a cutaway view of a distal portion of the handle of the suturing device of FIG. 3 exposing actuation mechanisms for deploying and retracting the suture snags with the actuation mechanisms shown in a refracted position.
Figure 11B:
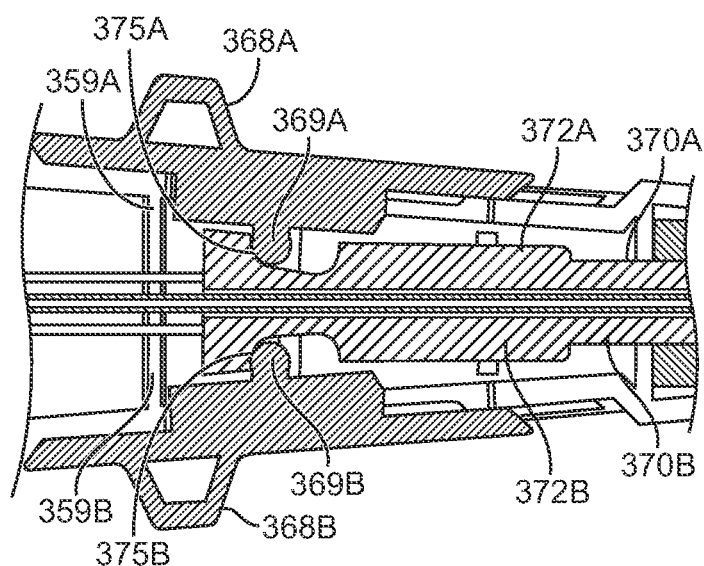
FIG. 11B is a sectional view of a portion of the handle of the suturing device of FIG. 3, wherein the handle portion includes actuation mechanisms for deploying and retracting the suture snags with the actuation mechanisms shown in a retracted position.

After respective ends of suture pairs 360A, 360B all extend into the lumen of the vessel and both needle pairs 356A, 356B have been retracted into elongated body 324 of the suturing device, suture snags 348A, 348B are proximally retracted to thereby capture the four extended suture ends and pull them into suturing device 320 as shown in FIG. 11. In order to retract suture snags 348A, 348B, actuators 368A, 368B are proximally retracted until bosses 369A, 369B thereof abut against and push proximal surfaces 375A, 375B of recesses 371A, 371B of transmission members 370A, 370B. By pushing transmission members 370A, 370B, suture snags 348A, 348B are thereby pushed or retracted back through openings 338 and into distal guiding component 332. Essentially, proximal ends 372A, 372B of transmission members 370A, 370B are returned to the position described above with respect to FIG. 4. Proximal ends 372A, 372B of transmission members 370A, 370B are proximally retracted until bosses 369A, 369B of actuators 368A, 368B, abut against stops 359A, 359B, respectively, of housing 323 of handle 322 that project radially inward to limit proximal retraction of actuators 368A, 368B. When the suture snags are retracted, suture pairs 360A, 360B extend out of ports 336 of distal guiding component 332, through tissue around the arteriotomy via the pathways or incisions created by needle pairs 356A, 356B, and then the ends of suture pairs 360A, 360B are captured within distal portion 335 of distal guiding component 332 as shown in FIG. 11. When captured, the ends of suture pairs 360A, 360B are pushed into catches or grips 339 of apertures 355 (see FIG. 6C) and therefore are tightly secured within apertures 355 of the suture snags.

Notably, other suturing devices known in the art utilize extendable needles to capture modified suture ends of a suture which have been delivered through an arteriotomy to a position within a vessel lumen. However, suturing device 320 positions ends of a suture through a vessel wall around an arteriotomy and then utilizes deployable suture snags to capture or catch the suture ends back into the suturing device. As such, suturing device 320 does not require modification of the suture ends for capture thereof. In addition, suturing device 320 improves consistency and reliability of capturing the suture ends.

At this point in the method of use, suturing device 320 having the captured suture ends therein is retracted until it is withdrawn from a patient so that a clinician gains access to second ends 364A, 364B of suture pairs 360A, 360B. More particularly, since suture pairs 360A, 360B are no longer coupled to suture holders 376A, 376B, respectively, and are instead slidingly positioned through retracted needle pairs 356A, 356B, suture pairs 360A, 360B slide through the needle pairs as the suturing device 320 (having first ends 362A, 362B captured therein) is retracted until second ends 364A, 364B of the suture pairs exit out of distal ends 358 of needle pairs 356A, 356B. The clinician then ties or forms at least one surgical knot 363 between the respective second ends of each suture pair, thereby forming a first elongated suture 361A from suture pair 360A and a second elongated suture 361B from suture pair 360B. In order to facilitate tying or forming the surgical knot between each pair of opposing suture ends, suture pair 360A may be formed from a different color and/or may be a different length than suture pair 360B so that the physician can easily identify the suture ends that are to be tied together. With reference to FIG. 12, which is a top view of vessel V having an arteriotomy $V_A$, newly formed elongated sutures 361A, 361B extend through the vessel wall around the arteriotomy and the opposing ends thereof (originally first ends 362A, 362B of suture pairs 360A, 360B) are still captured within suturing device 320. The clinician then pulls on or further proximally retracts suturing device 320 such that surgical knots 363 of elongated sutures 361A, 361B are positioned over the vessel wall and/or arteriotomy $V_A$ as shown in FIG. 12. The physician then cuts or severs elongated sutures 361A, 361B from suturing device 320. The physician may then pull one end of each elongated suture until surgical knots are accessible, i.e. located outside of the patient. A slip knot (not shown) is then tied below each surgical knot 363, and one end of each elongated suture 361A, 361B is pulled to move or slide each slip knot over the length of each elongated suture towards arteriotomy $V_A$. Hemostasis occurs when each slip knot abuts against the inside of the vessel wall, thereby closing or substantially closing the arteriotomy $V_A$ with a first stitch 393A and a second stitch 393B as shown in FIG. 13. FIG. 13 illustrates arteriotomy $V_A$ closed for illustrative purposes; however, if suturing device 320 is being utilized in a pre-closure technique, stitches 393A, 393B would seal the arteriotomy $V_A$ around an interventional device inserted through the arteriotomy $V_A$ as would be understood by one of ordinary skill in the art. The method steps described above for forming two stitches from suture pairs 360A, 360B are merely exemplary. Other devices or methods known in the art may be utilized to form two stitches from suture pairs 360A, 360B after suturing device 320 has captured the suture ends and thereby positioned the suture pairs through the vessel wall around the arteriotomy as desired. For example, although the above method illustrates forming two essentially parallel stitches 393A, 393B as shown in FIG. 13, different combinations of sutures may be tied together for forming the stitches, such as opposing sutures located 180 degrees from each other, to thereby form two stitches that crisscross in an "X" configuration. Stated another way, the elongated sutures 361A, 361B need not be formed from sutures of the same suture pair. Sutures of suture pair 360A may be tied to opposing sutures of suture pair 360B.

Figure 14A:
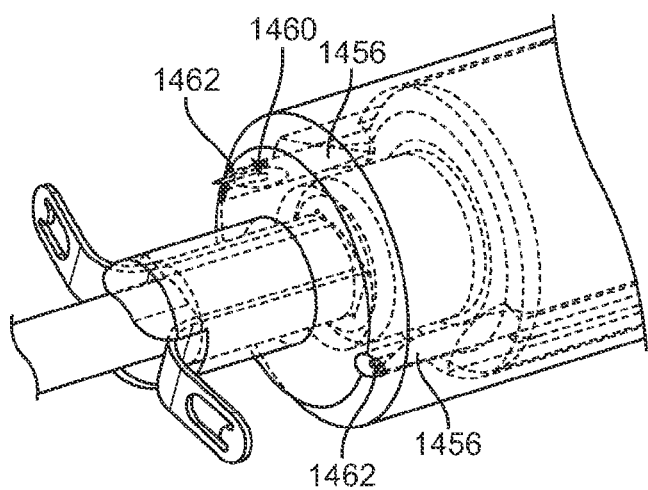
FIG. 14A is a perspective view of FIG. 14 showing the internal components in phantom.

In order to access smaller vessels, which have inherently smaller arteriotomies due to the relatively smaller diameters of the vessels themselves, it may be desirable to utilize a relatively smaller suturing device which delivers a single suture pair. FIGS. 14 and 15 illustrate an embodiment in which a suturing device 1420 includes a single suture snag 1448 and a single needle pair 1456 for delivering a single suture pair 1460. FIG. 14 and FIG. 14A are perspective views of a distal portion of suturing device 1420. As shown, suturing device 1420 includes an elongated body 1424 including an outer shaft 1426 and a distal guiding component 1432. Distal guiding component 1432 includes a distally tapered region that ends at an abutment surface 1434, and distal guiding component 1432 is utilized for guiding needle pair 1456 towards deployed suture snag 1448 having radially expandable distal arm portions 1451, 1453. A first suture of suture pair 1460 is housed within a first needle of needle pair 1456, and a second suture of suture pair 1460 is housed within a second needle of needle pair 1456. FIG. 14A illustrates first ends 1462 of suture pair 1460 housed within the distal ends of needle pair 1456.

Figure 15A:
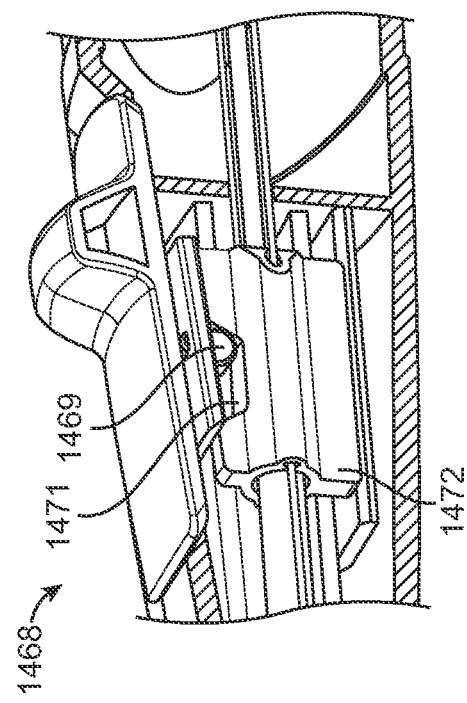
FIG. 15A is an enlarged sectional view of a distal portion of the handle of FIG. 15 illustrating an actuation mechanism for deploying the single suture snag.

FIG. 15 illustrates a sectional view of a handle 1422 of suturing device 1420, which deploys a single suture snag 1448 as well as only a single needle pair 1456 and single suture pair 1460. FIG. 15A is an enlarged sectional view of actuator 1468 for deploying and retracting suture snag 1448. As shown, similar to actuator 368, actuator 1468 includes a knob or boss 1469 which slidingly operates within a recess or groove 1471 of a proximal end 1472 of a transmission member 1470 which extends to and couples with a proximal end of suture snag 1448. Actuator 1468 distally advances or proximally retracts transmission member 1470, thereby distally advancing or proximally retracting suture snag 1448. FIGS. 15B, 15C, and 15D are views of actuator 1466 for extending and retracting needle pair 1456, as well as for extending suture pair 1460. As shown, similar to actuator 366, actuator 1466 includes a knob or boss 1467 which operates to distally advance a shuttle or carriage 1480. In the delivery configuration of the suturing device, a suture holder 1476 and a needle holder 1478 are both coupled to carriage 1480. Carriage 1480 includes a first leg 1497, a second leg 1499, which extends substantially parallel but spaced apart from first leg 1497, and a distal bridge 1479 which extends between the proximal ends of first and second legs 1497, 1499. Suture holder 1476 is positioned adjacent to and coupled to a distal portion of carriage 1480, between first and second legs 1497, 1499 thereof. Since suture holder 1476 is coupled to carriage 1480, carriage 1480 essentially pulls or carries suture holder 1476, and thus suture pair 1460 attached thereto, forward when carriage 1480 is distally advanced via actuator 1466. Needle holder 1478 includes a distal portion having claws or prongs 1482, which in this embodiment essentially clips or bosses to distal bridge 1479 of carriage 1480. Needle holder 1478 also includes a U-shaped proximal portion 1484A which includes a pair of channels or lumens 1490 formed there through for receiving needle pair 1456 and also includes a channel 1492 formed on an inner surface thereof for sliding or riding along inner shaft 1440. In a delivery configuration of the suturing device, needle holder 1478 is coupled to carriage 1480 via mating or bearing surfaces 1483 formed between prongs 1483 of the needle holder and distal bridge 1479 of the carriage. As a result of the interference fit between needle holder 1478 and carriage 1480 at bearing surfaces 1483, carriage 1480 pushes or carries needle holder 1478, and thus needle pair 1456 attached thereto, forward when carriage 1480 is distally advanced via actuator 1466 until the needle holder abuts against a stop 1485 of a housing 1423 of handle 1422. Needle holder 1478, as well as needle pair 1456 attached thereto, cannot be distally advanced any further but continued distal advancement of actuator 1466 results in continued distal advancement of carriage 1480, as well as suture holder 1476 and the ends of suture pair 1460. As best shown in FIG. 15C, continued distal advancement of carriage 1480 results in carriage 1480 overcoming the interference fit between bearing surfaces 1483 and thereby spreading or pushing apart distal prongs 1482 of needle holder 1478, thereby decoupling needle holder 1478 and carriage 1480 to allow the carriage to slidingly advance through or past the needle holder. As such, suture pair 1460 is distally advanced by continued movement of actuator 1466 while needle pair 1456 is not.

Figure 16:
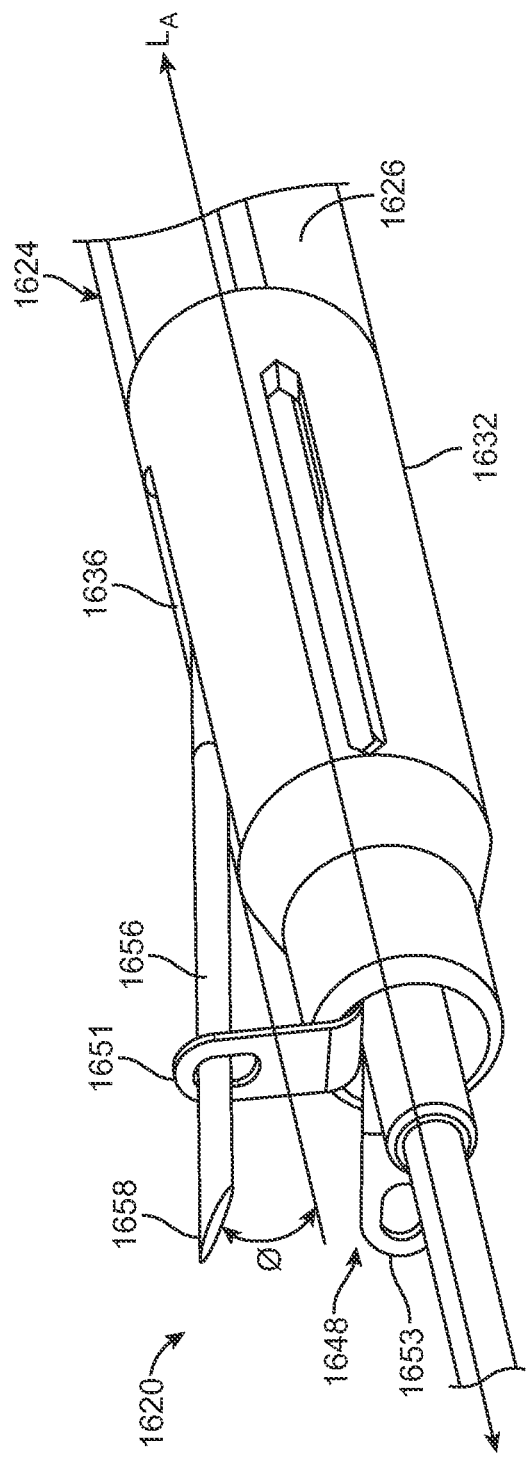
FIG. 16 is a perspective view of a distal end of a suturing device according to another embodiment hereof, wherein the suturing device includes needles that bend when extended from the suturing device.

In another embodiment hereof, in order to access smaller vessels, the size or outer diameter of the elongated body of the suturing devices described herein may be minimized by designing the plurality of needles to bend when being extended out of the distal guiding component. In an embodiment shown in FIG. 16, a suturing device 1620 includes an elongated body 1624 having an outer shaft 1626 and a distal guiding component 1632. Distal guiding component 1632 is utilized for guiding a needle pair 1656 towards deployed suture snag 1648 having radially extendable distal arm portions 1651, 1653. Only one suture snag is shown deployed in FIG. 16, and only one needle is shown for sake of clarity and illustration. In this embodiment, distal guiding component 1632 includes a plurality of side openings or ports 1636 in a wall thereof that each allow the needle associated therewith to be alternately extended and retracted therethrough. In a refracted position each needle is disposed within the elongated body and in an extended position each needle extends distally and radially outward from a longitudinal axis $L_A$ of elongated body 1624. As will be understood by one of ordinary skill in the art, the number of ports 1636 formed through distal guiding component 1632 corresponds to the number of needles located within the elongated body of suturing device 1620. When each needle pair 1656 is distally advanced, distal ends 1658 comes into contact with a curved deflection surface or edge formed within transverse port 1636 that operates to guide distal ends 1658 of each needle out of elongated body 1624 and causes each needle to bend radially outward at an acute angle relative to the longitudinal axis $L_A$ of elongated body 1624. As distal end 1658 exits from transverse port 1636, each needle gradually bends and assumes the extended position shown in FIG. 16 in which each needle extends distally and outwardly from elongated body 1624. In embodiment hereof, the angle θ of the needle deflection may be in a range of between 5 and 25 degrees. When needle pair 1656 is retracted back into elongated body 1624, they return to their original generally straight configurations since they are no longer in contact with the deflection surface of distal guiding component 1632 that caused the needles to bend radially outward in the extended position.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of positioning a suture at an arteriotomy of a vessel wall of a vessel, wherein the method includes the steps of:
    positioning a distal end of a suturing device through the arteriotomy, wherein the suturing device includes a handle and an elongated body coupled to a distal end of the handle;
    deploying at least one suture snag of the suturing device within the vessel from a retracted position in which two distal arm portions of the suture snag are disposed within the elongated body to a deployed position in which the two distal arm portions radially extend away from the elongated body;
    distally advancing at least one pair of needles of the suturing device from a loaded position in which the at least one pair of needles is disposed within the elongated body to a deployed position in which the at least one pair of needles distally extend from a distal end of the elongated body and penetrate through the vessel wall and through apertures of the two distal arm portions of the at least one deployed suture snag, wherein a suture is slidingly disposed through the lumen of each needle and each suture is concurrently carried with its respective needle during the step of extending the at least one pair of needles to the deployed position; and
    distally advancing the sutures relative to their respective needles from a loaded position in which a first end of each suture is disposed within its respective needle to a deployed position in which the first end of each suture extends distally away from the distal end of its respective needle.

2. The method of claim 1, further comprising the steps of:
    retracting the at least one pair of needles to a retracted position in which the at least one pair of needles is disposed within the elongated body, wherein the sutures remain in their deployed positions during the step of retracting the at least one pair of needles; and
    retracting the at least one suture snag to the retracted position, thereby pulling the first ends of the sutures into the elongated body of the suturing device.

3. The method of claim 2, wherein the first ends of the sutures are gripped within the apertures of the two distal arm portions after the at least one suture snag is retracted to the retracted position.

4. The method of claim 2, wherein the steps of deploying at least one suture snag and retracting the at least one suture snag are performed via a first actuation mechanism within the handle of the suturing device.

5. The method of claim 4, wherein the steps of distally advancing the at least one pair of needles, distally advancing the sutures, and retracting the at least one pair of needles are performed via a second actuation mechanism within the handle of the suturing device.

6. The method of claim 5, wherein the second actuation mechanism includes a suture holder and a needle holder, the at least one pair of needles being coupled to the needle holder and the sutures being coupled to the suture holder during the steps of distally advancing the at least one pair of needles and distally advancing the sutures and are disengaged from the suture holder after the step of retracting the at least one pair of needles.

7. The method of claim 6, wherein the second actuation mechanism also includes a carriage that is coupled to the suture holder, the needle holder being coupled to the carriage during the step of distally advancing the at least one pair of needles and being disengaged from the carriage after the step of distally advancing the at least one pair of needles.

8. The method of claim 1, wherein the step of positioning the distal end of the suturing device through the arteriotomy includes abutting an abutment surface of a distally tapered region of the suturing device against an outer surface of the vessel wall of the vessel.

9. The method of claim 1, wherein the step of deploying at least one suture snag of the suturing device includes extending the two distal arm portions of the suture snag out of openings at a distal end of the elongated body such that the at least one suture snag resumes its expanded deployed configuration.

10. The method of claim 1, wherein the needles are straight during the step of distally advancing the at least one pair of needles.

11. A method of positioning a suture at an arteriotomy of a vessel wall of a vessel, wherein the method includes the steps of:
positioning a distal end of a suturing device through the arteriotomy, wherein the suturing device includes a handle having a suture holder and a needle holder disposed within the handle and an elongated body coupled to a distal end of the handle;
deploying at least one suture snag of the suturing device within the vessel from a retracted position in which two distal arm portions of the suture snag are disposed within the elongated body to a deployed position in which the two distal arm portions radially extend away from the elongated body;
distally advancing at least one pair of needles of the suturing device from a loaded position in which the at least one pair of needles is disposed within the elongated body to a deployed position in which the at least one pair of needles distally extend from a distal end of the elongated body, wherein the at least one pair of needles is coupled to the needle holder and a suture is slidingly disposed through the lumen of each needle, a first end of each suture being disposed within its respective needle when the needle is in the loaded position, and wherein the sutures are coupled to the suture holder when the needles are in the loaded and deployed positions such that each suture is concurrently carried with its respective needle during the step of distally advancing the at least one pair of needles to the deployed position; and
distally advancing the sutures from a loaded position in which each first end of each suture is disposed within its respective needle to a deployed position in which the first ends of each suture extends distally away from the distal end of their respective needle, wherein the sutures are coupled to the suture holder and the needles remain in their deployed position during the step of distally advancing the sutures.

12. The method of claim 11, wherein the step of distally advancing the at least one pair of needles to the deployed position includes penetrating through the vessel wall and through apertures of the two distal arm portions of the at least one deployed suture snag.

13. The method of claim 12, further comprising the steps of:
retracting the at least one pair of needles to a retracted position in which the at least one pair of needles is disposed within the elongated body, wherein the sutures remain in their deployed positions during the step of retracting the at least one pair of needles and wherein the sutures decouple from the suture holder when the at least one pair of needles are in the retracted position; and
retracting the at least one suture snag to the retracted position, thereby pulling the first ends of the sutures into the elongated body of the suturing device.

14. The method of claim 13, wherein the first ends of the sutures are gripped within the apertures of the two distal arm portions after the at least one suture snag is retracted to the retracted position.

15. The method of claim 14, wherein the handle includes a carriage that is coupled to the suture holder, wherein the carriage is also coupled to the needle holder during the step of distally advancing the at least one pair of needles and is disengaged from the needle holder after the step of distally advancing the at least one pair of needles.

16. The method of claim 12, wherein the steps of deploying at least one suture snag and retracting the at least one suture snag are performed via a first actuation mechanism within the handle of the suturing device.

17. The method of claim 16, wherein the steps of distally advancing the at least one pair of needles, distally advancing the sutures, and retracting the at least one pair of needles are performed via a second actuation mechanism within the handle of the suturing device, the second actuation mechanism including the suture holder and the needle holder.

18. The method of claim 11, wherein the step of positioning the distal end of the suturing device through the arteriotomy includes abutting an abutment surface of a distally tapered region of the suturing device against an outer surface of the vessel wall of the vessel.

19. The method of claim 11, wherein the step of deploying at least one suture snag of the suturing device includes extending the two distal arm portions of the suture snag out of openings at a distal end of the elongated body such that the at least one suture snag resumes its expanded deployed configuration.

20. The method of claim 11, wherein the needles are straight during the step of distally advancing the at least one pair of needles.

* * * * *